(12) United States Patent
Knight

(10) Patent No.: US 11,000,851 B2
(45) Date of Patent: *May 11, 2021

(54) REAGENT WELL HAVING A RETENTION FEATURE FOR RETAINING A LYOPHILIZED REAGENT

(71) Applicant: GEN-PROBE INCORPORATED, San Diego, CA (US)

(72) Inventor: Byron J. Knight, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 44 days.

This patent is subject to a terminal disclaimer.

(21) Appl. No.: 15/677,364

(22) Filed: Aug. 15, 2017

(65) Prior Publication Data
US 2017/0341073 A1 Nov. 30, 2017

Related U.S. Application Data

(63) Continuation of application No. 14/210,127, filed on Mar. 13, 2014, now Pat. No. 10,654,041.
(Continued)

(51) Int. Cl.
*B01L 3/00* (2006.01)
*B65B 69/00* (2006.01)
(Continued)

(52) U.S. Cl.
CPC ............. *B01L 3/5085* (2013.01); *B01L 3/502* (2013.01); *B01L 3/5082* (2013.01);
(Continued)

(58) Field of Classification Search
CPC .......... B01L 3/52; B01L 3/527; B01L 3/5082; B01L 3/5085; B01L 3/50853; B01L 2200/16; B01L 2300/0858
See application file for complete search history.

(56) References Cited

U.S. PATENT DOCUMENTS 3,785,773 A 1/1974 Rohrbaugh
4,162,003 A 7/1979 Bartos
(Continued)

FOREIGN PATENT DOCUMENTS

CA 1035260 A 7/1978
CN 101219298 A 7/2008
(Continued)

OTHER PUBLICATIONS

International Search Report and Written Opinion issued in International Patent Application No. PCT/US2014/026789 (dated Oct. 15, 2014).
(Continued)

*Primary Examiner* — Jill A Warden
*Assistant Examiner* — Dwayne K Handy
(74) *Attorney, Agent, or Firm* — Rothwell, Figg, Ernst & Manbeck, P.C.; Charles B. Cappellari

(57) ABSTRACT

A method for reconstituting a lyophilized reagent contained within a reagent well comprises the steps of drawing a diluent into a pipette tip attached to an automated pipettor and dispensing the diluent into the reagent well containing the lyophilized reagent. The reagent well has an internal side wall, a bottom wall, and an open upper end and includes one or more retention features disposed about the periphery of the internal side wall and defining a central opening into the well that permits passage of the pipette tip into the reagent well. The one or more retention features are integrally formed with the internal side wall, and each of the one or more retention features extends over a portion of the lyophilized reagent, thereby retaining the lyophilized reagent within the reagent well.

13 Claims, 28 Drawing Sheets

Related U.S. Application Data

(60) Provisional application No. 61/782,320, filed on Mar. 14, 2013.

(51) Int. Cl.
| | | |
|---|---|---|
| *G01N 35/10* | (2006.01) | |
| *B65D 39/00* | (2006.01) | |
| *G01N 35/02* | (2006.01) | |
| *C12Q 1/686* | (2018.01) | |
| *B65D 1/02* | (2006.01) | |
| *B65D 1/34* | (2006.01) | |
| *B65D 1/36* | (2006.01) | |
| *B65D 17/50* | (2006.01) | |
| *G01N 35/00* | (2006.01) | |
| *G01N 30/60* | (2006.01) | |

(52) U.S. Cl.
CPC ....... *B01L 3/50825* (2013.01); *B01L 3/50853* (2013.01); *B01L 3/50855* (2013.01); *B01L 3/523* (2013.01); *B01L 3/527* (2013.01); *B65B 69/00* (2013.01); *B65D 1/0207* (2013.01); *B65D 1/34* (2013.01); *B65D 1/36* (2013.01); *B65D 17/50* (2013.01); *B65D 39/0017* (2013.01); *B65D 39/0029* (2013.01); *C12Q 1/686* (2013.01); *G01N 35/0099* (2013.01); *G01N 35/026* (2013.01); *G01N 35/10* (2013.01); *G01N 35/1002* (2013.01); *G01N 35/1079* (2013.01); *B01L 2200/02* (2013.01); *B01L 2200/025* (2013.01); *B01L 2200/026* (2013.01); *B01L 2200/0668* (2013.01); *B01L 2200/0689* (2013.01); *B01L 2200/141* (2013.01); *B01L 2200/142* (2013.01); *B01L 2200/16* (2013.01); *B01L 2300/042* (2013.01); *B01L 2300/044* (2013.01); *B01L 2300/046* (2013.01); *B01L 2300/047* (2013.01); *B01L 2300/048* (2013.01); *B01L 2300/0609* (2013.01); *B01L 2300/0829* (2013.01); *B01L 2300/0832* (2013.01); *B01L 2300/0838* (2013.01); *B01L 2300/0851* (2013.01); *B01L 2300/0858* (2013.01); *B01L 2300/12* (2013.01); *B01L 2400/0406* (2013.01); *B65D 2539/003* (2013.01); *G01N 30/6091* (2013.01); *G01N 2035/00287* (2013.01); *Y10T 436/11* (2015.01)

(56) References Cited

U.S. PATENT DOCUMENTS

| | | | |
|---|---|---|---|
| 6,143,250 A | 11/2000 | Tajima | |
| 6,241,949 B1 | 6/2001 | Kane | |
| 6,346,421 B1 | 2/2002 | Anderson et al. | |
| 9,718,059 B2 | 8/2017 | Buse et al. | |
| 9,817,011 B2 * | 11/2017 | Buse | B65D 1/0207 |
| 10,478,820 B2 * | 11/2019 | Knight | B01L 3/5085 |
| 2005/0271553 A1 | 12/2005 | Ramstad | |
| 2006/0013031 A1 | 1/2006 | Ravkin | |
| 2007/0202538 A1 | 8/2007 | Glezer | |
| 2009/0311775 A1 | 12/2009 | Kocourek et al. | |
| 2011/0027914 A1 | 2/2011 | Bunce et al. | |

FOREIGN PATENT DOCUMENTS

| | | |
|---|---|---|
| CN | 202778533 U | 3/2013 |
| DE | 102005062052 A1 | 6/2007 |
| EP | 1757679 A1 | 2/2007 |
| EP | 1911519 A2 | 4/2008 |
| EP | 2073017 A1 | 6/2009 |
| FR | 2281768 A1 | 3/1976 |
| WO | WO 8904487 A1 | 5/1989 |
| WO | WO 0012675 A1 | 3/2000 |
| WO | WO 03042697 A1 | 5/2003 |
| WO | WO 2009153348 A2 | 12/2009 |
| WO | 2012/012779 A2 | 1/2012 |

OTHER PUBLICATIONS

International Preliminary Report on Patentability issued in International Patent Application No. PCT/US2014/026789 (dated Sep. 15, 2015), 26 pages.
Non-final Office Action issued in U.S. Appl. No. 14/210,127, 56 pages. (dated Jul. 1, 2016).
Final Office Action issued in U.S. Appl. No. 14/210,127, 10 pages (dated Jan. 13, 2017).
Non-final Office Action issued in U.S. Appl. No. 14/210,127, 12 pages (dated Oct. 12, 2017).
Non-final Office Action issued in U.S. Appl. No. 15/339,347, 8 pages (dated Sep. 22, 2017).
EPO Communication pursuant to Article 94(3) EPC, European Application No. 17190591.2, dated Feb. 5, 2019.
Final Office Action dated Apr. 19, 2018 issued in U.S. Appl. No. 15/339,347. (13 pages).
Final Office Action dated May 3, 2018 issued in U.S. Appl. No. 14/210,127. (11 pages).
Advisory Action dated Jun. 28, 2018 issued in U.S. Appl. No. 15/339,347. (4 pages).
USPTO Office Action, U.S. Appl. No. 15/339,347, dated Apr. 18, 2019.
Notice of Allowance, U.S. Appl. No. 15/339,347, dated Jul. 10, 2019.
CIPO Office Action, Canadian Application No. 2,936,223, dated Aug. 16, 2016.
CIPO Office Action, Canadian Application No. 2,936,223, dated Jul. 12, 2018.
CIPO Notice of Allowance, Canadian Application No. 2,936,223, dated Sep. 23, 2019.
SIPO First Office Action, Chinese Application No. 201910116937.8, dated Jan 19, 2021.
SIPO Search Report, Chinese Application No. 201910116937.8, dated Jan. 13, 2021.

* cited by examiner

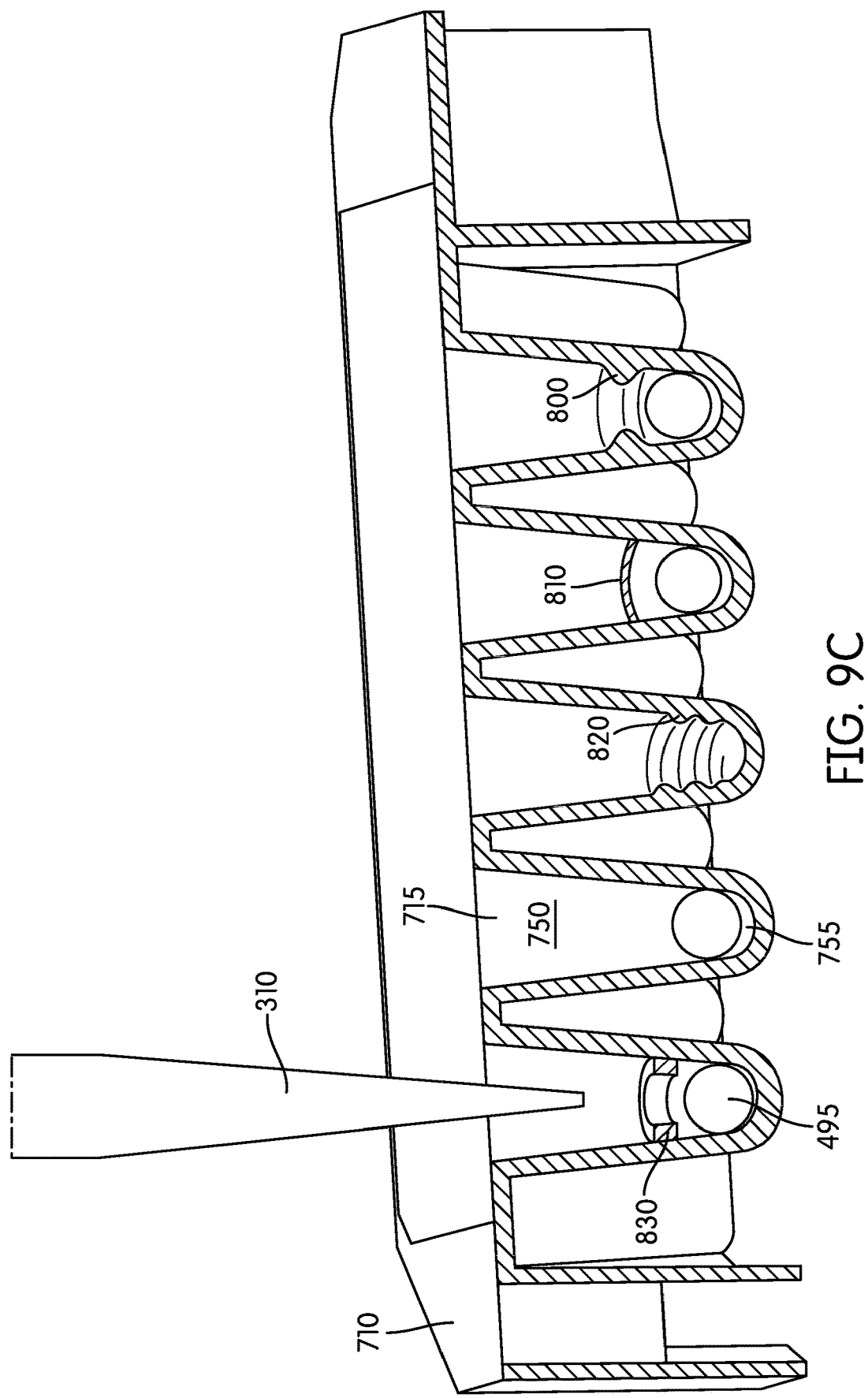

REAGENT WELL HAVING A RETENTION FEATURE FOR RETAINING A LYOPHILIZED REAGENT

CROSS REFERENCE TO RELATED APPLICATION

This application claims the benefit under 35 U.S.C. § 120 of the filing date of non-provisional patent application Ser. No. 14/210,127 filed Mar. 13, 2014, which claims the benefit under 35 U.S.C. § 119(e) of the filing date of U.S. Provisional Application No. 61/782,320, filed Mar. 14, 2013, which is incorporated herein by reference.

BACKGROUND

Field

The present disclosure relates to systems and apparatuses for performing automated reagent-based biochemical assays.

Background Information

Automated molecular assay instrumentation offers numerous advantages, however most automated instruments suffer from a limited set of assay capabilities. These limited capabilities complicate or inhibit parallel processing of multiple assays and, as a result, reduce sample throughput and flexibility in assay choices. This is particularly true for sensitive assays such as those involving nucleic acid detection and/or an amplification procedure. There are many procedures in use for amplifying nucleic acids, including the polymerase chain reaction (PCR), (see, e.g., Mullis, "Process for Amplifying, Detecting, and/or Cloning Nucleic Acid Sequences," U.S. Pat. No. 4,683,195), transcription-mediated amplification (TMA), (see, e.g., Kacian et al., "Nucleic Acid Sequence Amplification Methods," U.S. Pat. No. 5,399,491), ligase chain reaction (LCR), (see, e.g., Birkenmeyer, "Amplification of Target Nucleic Acids Using Gap Filling Ligase Chain Reaction," U.S. Pat. No. 5,427,930), strand displacement amplification (SDA), (see, e.g., Walker, "Strand Displacement Amplification," U.S. Pat. No. 5,455,166), and loop-mediated isothermal amplification (see, e.g., Notomi et al., "Process for Synthesizing Nucleic Acid," U.S. Pat. No. 6,410,278). A review of several amplification procedures currently in use, including PCR and TMA, is provided in HELEN H. LEE ET AL., NUCLEIC ACID AMPLIFICATION TECHNOLOGIES (1997).

Automated molecular assays incorporate the use of consumable components, which may or may not hold reagents utilized in the molecular assay to be performed, which can be manually loaded onto automated instrumentation. Providing such consumable components that are configured to limit contamination, enhance target detection, simplify loading into and transport within the system, enhance the operability of mechanical components within the automated system while lowering cost, and providing high performance in connection with the assay to be performed is desirable.

The present disclosure addresses these and other needs in the art.

All documents referred to herein, or the indicated portions, are hereby incorporated by reference herein. No document, however, is admitted to be prior art to the claimed subject matter.

SUMMARY

The present disclosure relates to systems, methods, and apparatuses for performing automated reagent-based biochemical assays.

Accordingly, in an aspect of the present disclosure, there is provided a single-piece receptacle. The receptacle includes a body having a generally cylindrical upper portion and a tapered lower portion, the upper portion having an open end and the lower portion being closed-ended, an annular ring formed on an outer surface of the body, the annular ring separating the upper and lower portions of the body, a lip circumscribing the open end of the upper portion, the lip being adapted for inter-locking engagement with a mated cap, and a plurality of longitudinally oriented grooves formed in an inner surface of the upper portion of the body and situated between the open end and the annular ring. In various embodiments, the closed end of the lower portion may be flat or curved. The number of grooves disposed on the inner surface of the upper portion is selected from the group consisting of 2, 3, 4, 5, 6, 7, and 8. The lip may radially-extend from an exterior surface of the upper portion and tapers towards the open end thereof.

In another aspect, the disclosure provides a cap securable to the single-piece receptacle. The cap includes a lower portion having an outer surface for sealing engagement of an inner surface of the open upper end of the body, the outer surface including one or more annular ring(s), an upper portion having a length, an inner surface, an outer surface, and an open end configured for engagement with an automated pipettor, and further including one or more recess(es), which can be concave in shape, disposed on the outer surface thereof extending along at least part of the length of the upper portion, and one or more linear rib(s) disposed on the inner surface of the upper portion, each linear rib having a length corresponding to the length of at least one of the recesses, and wherein each of the one or more linear ribs is positioned on the inner surface of the cap in a manner that corresponds to at least one of the recesses such that at least one linear rib lies on an inner surface of the cap that directly opposes the position of at least one recess on the outer surface of the cap, and a lip positioned between, and extending radially away from, the upper and lower portions, the lip including a plurality of locking arms extending toward the lower portion of the cap for securely engaging the lip of the receptacle. In various embodiments, the number of linear ribs corresponds to the number of recesses in a one-to-one relationship, and the number of recesses disposed on the outer surface of the cap is selected from the group consisting of 2, 3, 4, 5, 6, 7, and 8. The lower portion of the cap may include 1, 2, or 3 annular rings for sealing engagement of the inner surface of the body of the receptacle.

In certain embodiments, the locking arms comprise a snap fit attachment for securely engaging the lip of the receptacle. The number of locking arms may be selected from the group consisting of 1, 2, 3, 4, 5, 6, 7, and 8. In addition, the number of linear ribs disposed on the inner surface of the upper portion of the cap may be selected from the group consisting of 2, 3, 4, 5, 6, 7, and 8. The distal portion of the cap may further include a bottom separating the upper portion of the cap from the proximal lower portion of the cap. In certain embodiments, the bottom is scored for piercing. The at least one of the linear rib includes a portion that gradually tapers radially inward toward the center of the upper portion, or increases in size (e.g., an increase in thickness or radial geometry) as the at least one of the linear ribs approaches the bottom separating the upper portion of the cap from the proximal lower of the cap.

In another aspect, the disclosure provides a method for the automated removal of a cap from a capped reaction receptacle. The method includes providing a single-piece receptacle comprising a body having a generally cylindrical upper portion and a tapered lower portion, the upper portion having an open end and the lower portion being closed-ended; an annular ring formed on an outer surface of the body, the annular ring separating the upper and lower portions of the body; a lip circumscribing the open end of the upper portion, the lip being adapted for inter-locking engagement with a mated cap; and a plurality of longitudinally oriented grooves formed in an inner surface of the upper portion of the body and situated between the open end and the annular ring; and a cap securable to the single-piece receptacle, comprising: a lower portion having an outer surface for sealing engagement of an inner surface of the open upper end of the body, the outer surface including one or more annular ring(s); an upper portion having a length, an inner surface, an outer surface, and an open end configured for engagement with an automated pipettor, and further including one or more recess(es) disposed on the outer surface thereof extending along at least part of the length of the upper portion, and one or more linear rib(s) disposed on the inner surface of the upper portion, each linear rib having a length corresponding to the length of at least one of the recesses, and wherein each of the one or more linear ribs is positioned on the inner surface of the cap in a manner that corresponds to at least one of the recesses such that at least one linear rib lies on an inner surface of the cap that directly opposes the position of at least one recess on the outer surface of the cap; and a lip positioned between, and extending radially away from, the upper and lower portions, the lip including a plurality of locking arms extending toward the lower portion of the cap for securely engaging the lip of the receptacle. The cap is securely engaged to the single piece receptacle. The method further includes performing an automated motion of contacting an inner portion of at least one of the plurality of locking arms with a raised annular ridge defined around a receptacle slot, wherein said contacting urges the locking arms away from the lip of the receptacle thereby disengaging the cap from the receptacle, and while the cap is disengaged from the receptacle, performing an automated motion of lifting the cap away from the receptacle, thereby removing the cap from the capped reaction receptacle.

In another aspect, the disclosure provides a multi-well tray for use in an automated process. The multi-well tray includes a base having a top surface, a card insert having a first surface, the card insert configured for removable attachment to the base, wherein when attached to the base, the first surface of the card insert is substantially parallel to and flush with the top surface of the base, and a plurality of sets of wells. Each set of wells includes a first well disposed in an opening of the top surface of the base, the first well being configured to receive a receptacle cap, second well disposed in an opening of the top surface of the base, the second well being configured to receive a receptacle, wherein the receptacle cap and the receptacle are configured for secure engagement with each other, and a third well disposed in an opening of the first surface of the card insert, the third well containing a lyophilized reagent. The wells of each set of wells are disposed in alignment with each other, and the third well is sealed with a frangible seal. In certain embodiments the third well may include one or more retention features for retaining a lyophilized reagent at the bottom thereof.

In another aspect, the disclosure provides a reagent-containing multi-well tray for use in an automated process. The multi-well tray includes a base having a top surface and a plurality of wells disposed therein. Each of the wells may be defined by a cylindrical or conical wall, an open upper end, and a bottom. The wells may be disposed in alignment with each other, and sealed with a frangible seal. In certain embodiments each of the wells may include at least one retention feature to retain a lyophilized reagent therein. The multi-well tray may further include a lyophilized reagent disposed within each well, positioned at, or adjacent to, the bottom. Exemplary retention features include, but are not limited to, an annular ridge formed on the well wall and positioned above the lyophilized reagent, a spiral channel formed along a length of the well wall and positioned above the lyophilized reagent, a tapered ring attached to the well wall and positioned above the lyophilized reagent, a capillary insert attached to the well wall, and a collar attached to the well wall at or proximal to the open upper end. The collar may further include one or more fingers formed on a bottom surface thereof that protrude along a radius of curvature toward an axial center of the well. The capillary insert may include an open upper end that tapers toward the bottom of the well, and a capillary channel formed between the open upper end and the bottom of the well. In certain embodiments, the lyophilized reagent is held in position at, or adjacent to, the bottom through the use of electrostatic force.

In various aspects, any of the multi-well trays may also include machine readable indicia positioned on the base or card insert containing identifying information regarding the multi-well tray or card insert, including reagents contained therein. The machine readable indicia may be a barcode, 2D barcode, or a radio frequency identification (RFID). In addition, the multi-well tray may include one or more locking arms disposed on the card insert for locking engagement with the base. The first well may be defined by a first side wall and a bottom surface, and include a protrusion extending from a center of the bottom surface of the well toward the top surface of the base for frictional engagement with a hollow portion in the lower portion of the receptacle cap. The first well may also include a plurality of tabs protruding from the first side wall for securely engaging the receptacle cap. The second well may be defined by a second side wall and a second bottom, the second bottom including a through-hole extending from an inner surface of the second well to an outer surface of the base. An annular ledge may then be formed within the second well at the circumference of the through-hole. The second well may also include a plurality of legs protruding from the second side wall for securely engaging the distal portion of the cap. The third well may be defined by a third side wall and a third bottom, and include one or more features selected from the group consisting of a convex groove, a concave groove, and a set of grooves comprising a criss-cross pattern disposed in the third bottom. The third side wall may be conical, tapering toward the bottom thereof. The third well may also include a plurality of rigid guides radially protruding from the third wall toward a center thereof. The base may be spatially indexed such that an automated pipettor can accurately identify and/or access any of the plurality of wells when the multi-well tray is placed in an automated system.

In another aspect, the disclosure provides a cartridge with communicating wells for use in an automated process. The cartridge includes a casing having a top surface, a fluid chamber disposed within the casing, and wherein a first opening is provided in the top surface of the casing having at least one side wall surface extending to, or optionally forming at least a portion of, the fluid chamber, and a fluid reservoir disposed within the casing adjacent to and in fluid communication with the fluid chamber. In certain embodiments, the cartridge also includes an oil reservoir disposed within the casing and adjacent to the fluid chamber. The fluid communication between the fluid chamber and the fluid reservoir may be both liquid and gaseous communication, and may be provided by the same or different means. The cartridge may also include a second opening that is provided in the top surface of the casing having at least one side wall surface extending to, or optionally forming at least a portion of, the fluid reservoir. Each of the first and second openings may be sealed from exposure to the ambient atmosphere with a frangible seal.

In another aspect, the disclosure provides a cartridge rack for use in an automated process. The cartridge rack includes a chassis having a top surface and a first and a second opposing end, the chassis being configured for releasable attachment to one or more multi-well trays(s) as set forth herein, a plurality of machine readable indicia including data disposed on the chassis, and a handle disposed on the first end surface of the chassis. The chassis is configured for releasable attachment to a plurality (e.g., two or more, or up to five) multi-well trays. In various embodiments, the chassis is configured for releasable attachment to a cartridge with communicating wells. As discussed above, the cartridge includes a casing having a top surface; a fluid chamber disposed within the casing, and wherein a first opening is provided in the top surface of the casing having at least one side wall surface extending to, or optionally forming at least a portion of, the fluid chamber; and a fluid reservoir disposed within the casing adjacent to and in fluid communication with the fluid chamber. The machine readable indicia may include identifying information regarding the multi-well tray attached thereto, and may be in the form of a barcode, 2D barcode, QR code, or an RFID. The machine readable indicia may be readable through a direct contact connection, a wired connection, or wirelessly.

In another aspect, the disclosure provides a system for conducting an automated reagent-based assay. The system includes a multi-well tray, a cartridge with communicating wells, and an automated pipettor positioned on a robot arm. The multi-well tray may include a plurality of wells, each of the wells containing a lyophilized reagent, wherein the plurality of wells are disposed in alignment with each other and sealed with a frangible seal, wherein the lyophilized reagent includes a target-specific reagent. The cartridge with communicating wells includes a casing having a top surface; a fluid chamber disposed within the casing, and wherein a first opening is provided in the top surface of the casing having at least one side wall surface extending to, or optionally forming at least a portion of, the fluid chamber; a fluid reservoir disposed within the casing in fluid communication with the fluid chamber; and a diluent contained within the fluid chamber. The automated pipettor is adapted to execute a retrieval and dispense protocol that includes a retrieval of a portion of the reagent from the cartridge and a dispense of the portion of the reagent in one of the plurality of wells, and wherein the retrieval and dispense protocol is repeated for each of the plurality of wells. In various embodiments, the multi-well tray, the cartridge with communicating wells, and the automated pipettor are contained within a housing, such as an automated biochemical analyzer.

In another aspect, the disclosure provides a method for providing a stabilized reagent for a molecular assay. The method includes introducing a fluid molecular assay reagent to a well, the well including a tapered opening and a capillary insert having a capillary channel, wherein the tapered opening and capillary channel are in fluid communication. Thereafter, subjecting the well containing the reagent to conditions suitable for lyophilizing the fluid molecular assay reagent to prepare a lyophilized reagent. Thereafter, reconstituting the lyophilized reagent by introducing a reconstitution solution to the tapered opening of the well to prepare a reconstituted reagent. Then withdrawing the reconstituted reagent using a fluid transfer device that is introduced into the tapered opening of the well. In various embodiments, the fluid transfer device is a pipettor. The molecular assay may be a polymerase chain reaction (PCR) assay.

BRIEF DESCRIPTION OF THE DRAWINGS

FIG. 1A is a side view of the receptacle. FIG. 1B is a cross-sectional view of the receptacle taken along the line 1B-1B in FIG. 1A. FIG. 1C top view of the receptacle. FIG. 1D is a perspective view of the receptacle.

FIG. 2A is a side view of the cap. FIG. 2B is a cross-sectional view of the cap taken along the line 2B-2B in FIG. 2A. FIG. 2C top view of the cap. FIG. 2D is a bottom view of the cap. FIGS. 2E and 2F are top and bottom perspective views of the cap.

FIGS. 5B-5E show various views of inner surfaces of the wells of the card insert.

FIGS. 9A-9E are pictorial diagrams showing alternative configurations of a multi-well tray and various exemplary embodiments of inner surfaces of the wells therein.

DETAILED DESCRIPTION

Figure 1A:
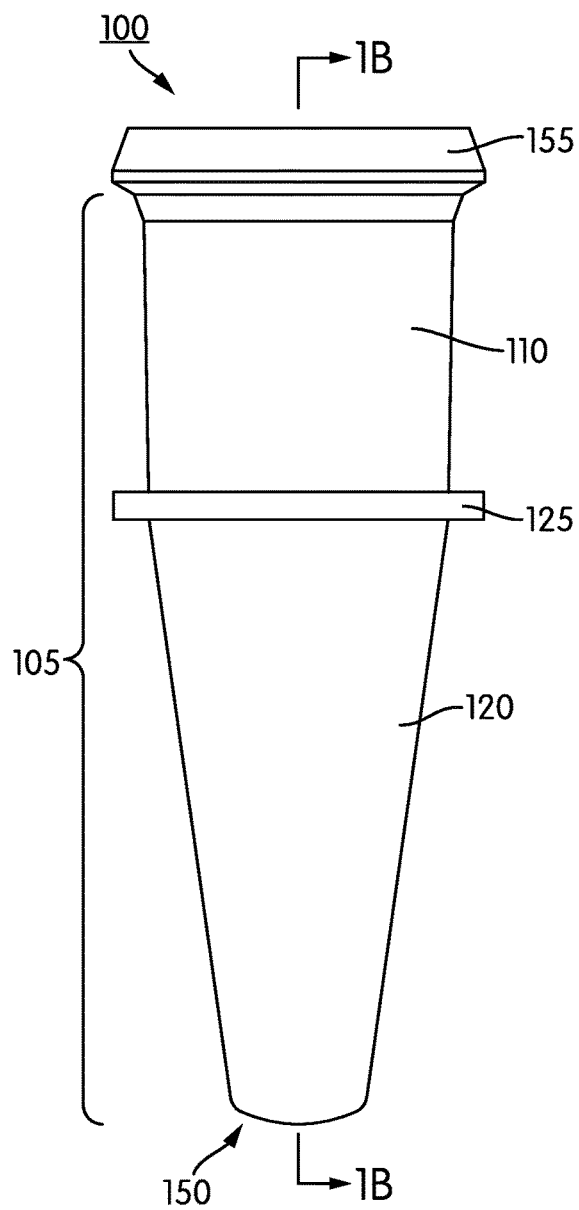
FIGS. 1A-1D are pictorial diagrams showing a receptacle of the present disclosure.
Figure 1B:
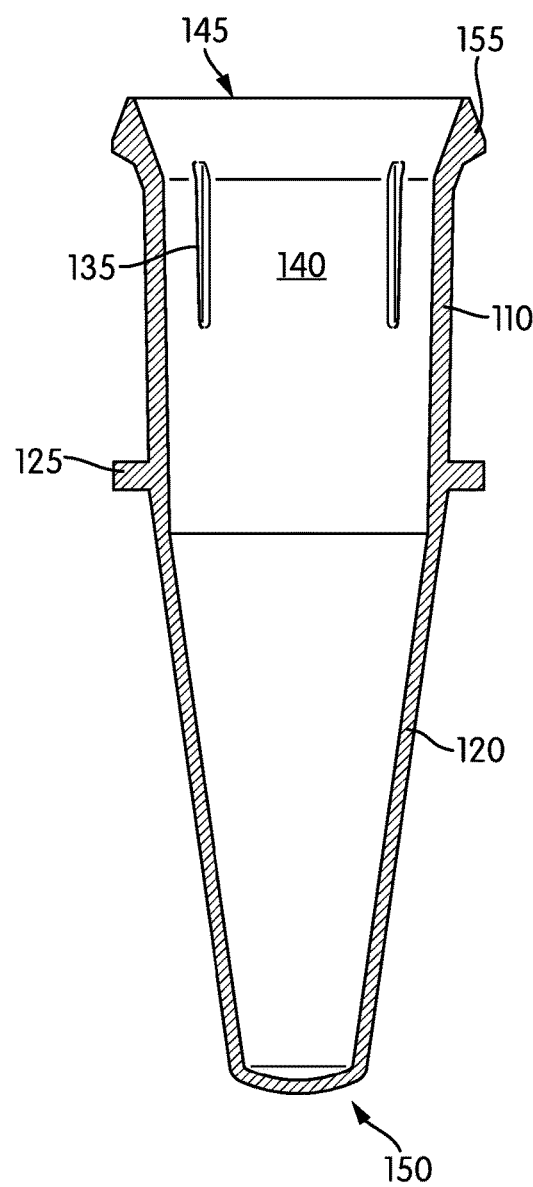
Figure 1C:
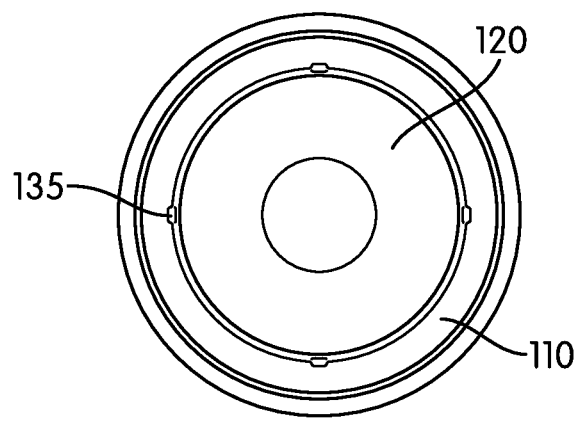
Figure 1D:
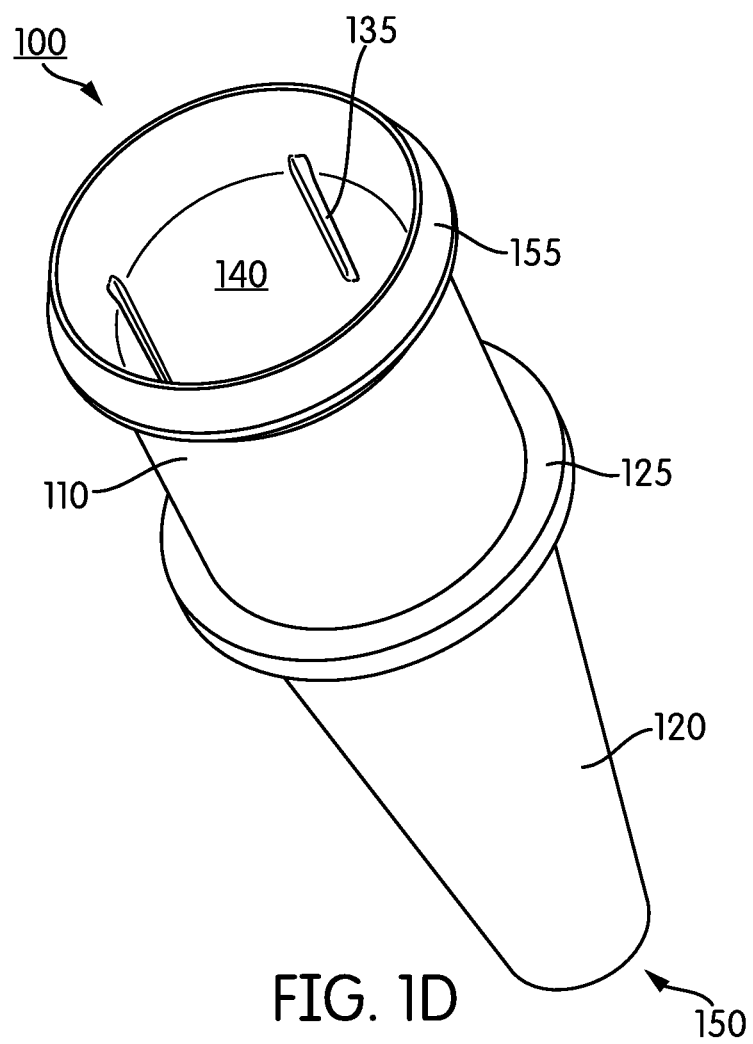
Figure 2A:
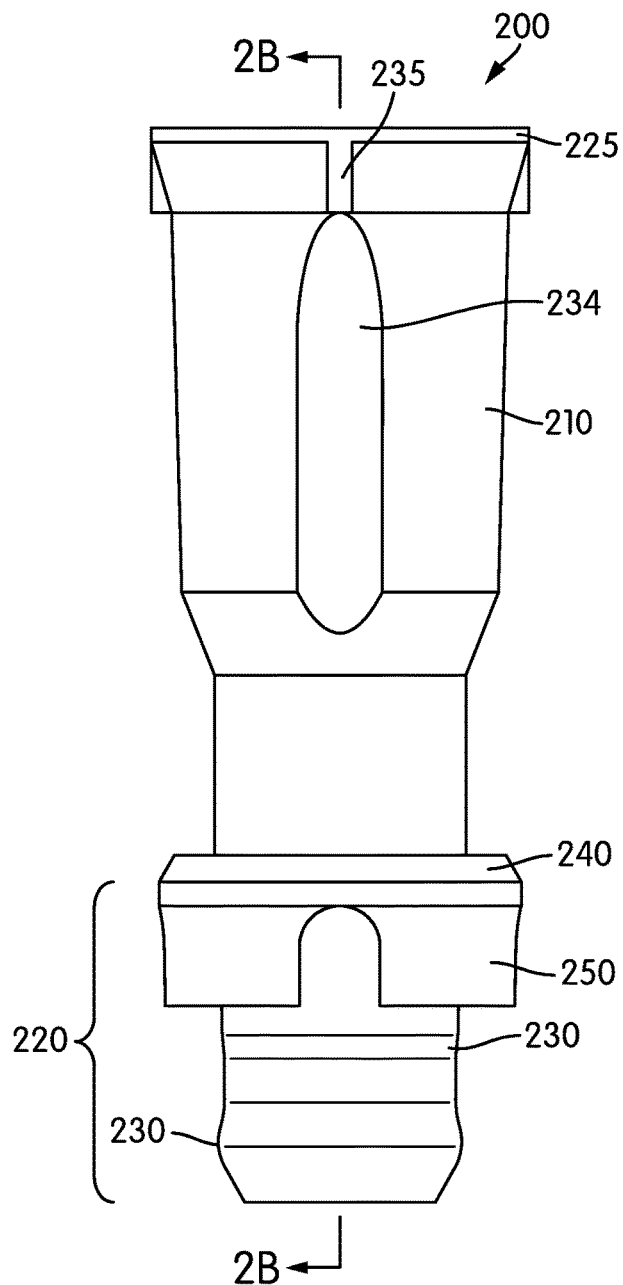
FIGS. 2A-2F are pictorial diagrams showing a cap of the present disclosure.
Figure 2B:
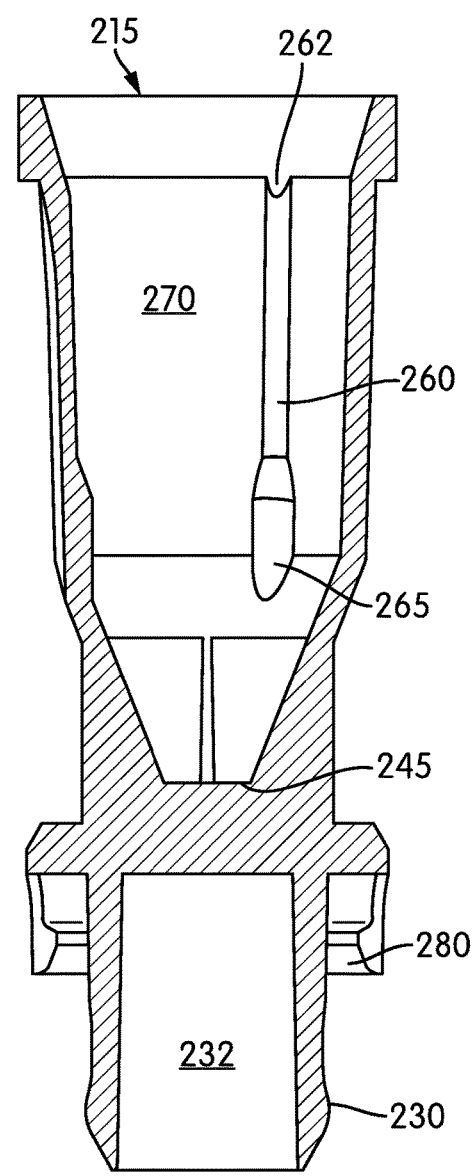
Figure 2C:
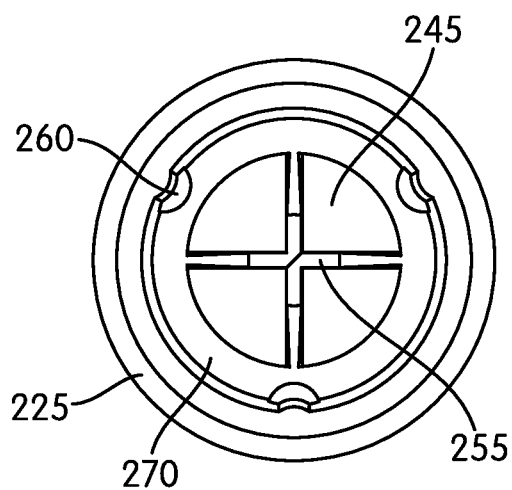
Figure 2D:
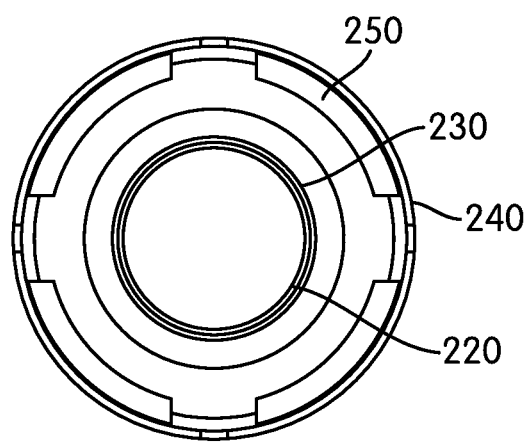
Figure 2E:
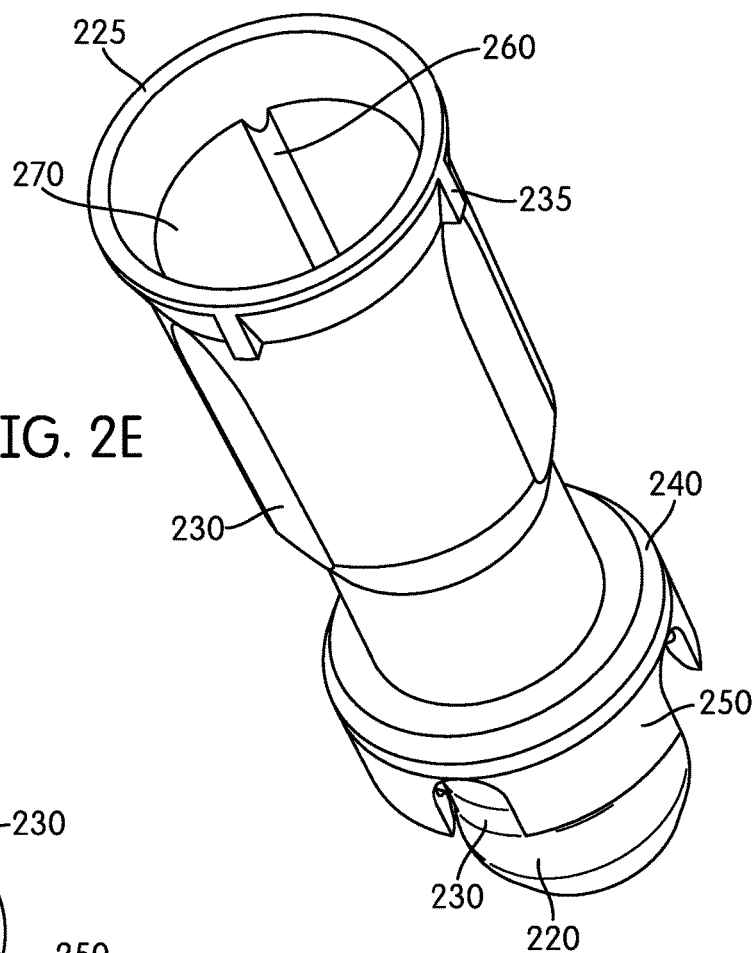
Figure 2F:
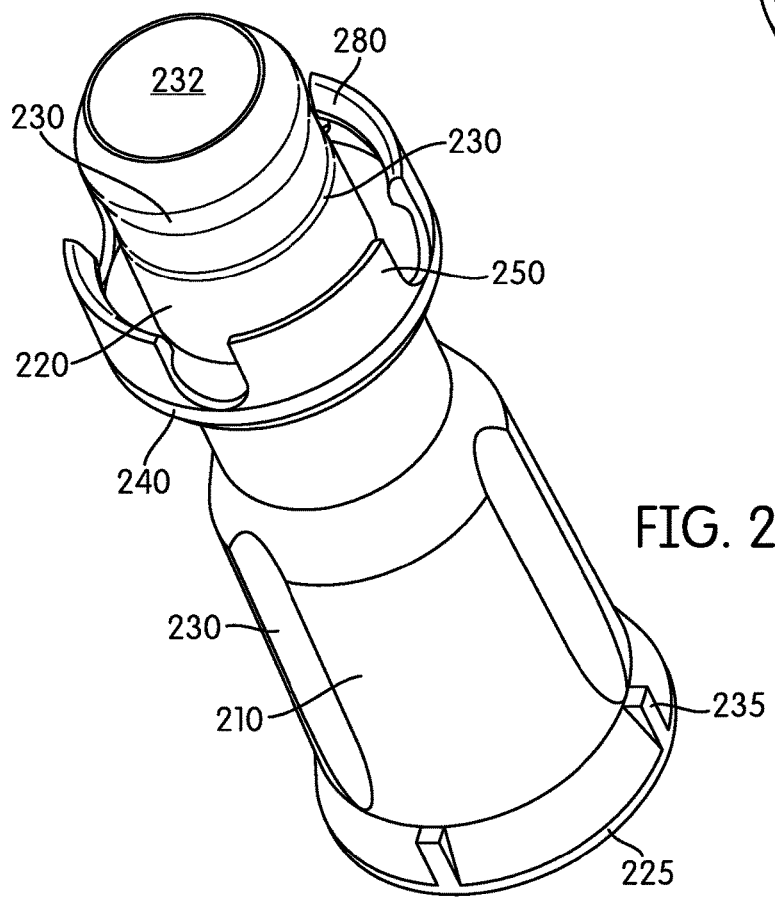

The present disclosure relates to a system, apparatus, and method for automated processing of a sample receptacle holder that is adapted for use in an automated instrument capable of performing nucleic acid-based amplification assays. Also provided are methods for conducting automated, random-access temperature cycling processes using the same.

Before the present systems, methods, and apparatuses are described, it is to be understood that this disclosure is not limited to particular methods and experimental conditions described, as such methods and conditions may vary. It is also to be understood that the terminology used herein is for purposes of describing particular embodiments only, and is not intended to be limiting, since the scope of the present disclosure will be limited only in the appended claims.

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," "having," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the disclosed subject matter. The present disclosure contemplates exemplary embodiments of an apparatus and methods of use thereof corresponding to the scope of each of these phrases. Thus, an apparatus or method comprising recited elements or steps contemplates particular embodiments in which the apparatus or method consists essentially of or consists of those elements or steps.

Unless defined otherwise, all technical and scientific terms used herein have the same meaning as commonly understood by one of ordinary skill in the art to which this disclosure belongs. Although any methods and materials similar or equivalent to those described herein can be used in the practice or testing disclosed herein, the preferred methods and materials are now described.

As used herein, a "reaction mixture" refers to a volume of fluid comprising one or more of a target-specific reagent, diluent for reconstituting a lyophilized reagent, one or more nucleotides, an enzyme, and a sample containing or suspected of containing a nucleic acid.

As used herein, a "sample" or a "test sample" refers to any substance suspected of containing a target organism or biological molecule, such as nucleic acid. The substance may be, for example, an unprocessed clinical specimen, a buffered medium containing the specimen, a medium containing the specimen and lytic agents for releasing nucleic acid belonging to the target organism, or a medium containing nucleic acid derived from a target organism which has been isolated and/or purified in a reaction receptacle or on a reaction material or device. In some instances, a sample or test sample may comprise a product of a biological specimen, such as an amplified nucleic acid to be detected.

As used herein, the term "biochemical assay" refers to a scientific investigative procedure for qualitatively assessing or quantitatively measuring the presence or amount or the functional activity of a target entity, such as, but not limited to, a biochemical substance, a cell, organic sample, or target nucleic acid sequence. Included in the term "biochemical assay" are nucleic acid amplification and heat denaturation (i.e., melting). Nucleic acid melting typically involves precise warming of a double stranded nucleic acid molecule to a temperature at which the two strands separate or "melt" apart. The melting process typically occurs at a temperature of about 50° C. to about 95° C.

As used herein, the term "lyophilization" refers to a dehydration process that is typically used to preserve a perishable material and/or facilitate transport thereof. Thus, "conditions for lyophilization" refer to subjecting a liquid material and/or a vessel containing the liquid material to freezing conditions while reducing the surrounding pressure to allow the frozen water within the material to sublimate directly from the solid phase to the gas phase. Such freezing conditions may include cooling the material below the lowest temperature at which the solid and liquid phases thereof can coexist (known in the art as the "triple point"). Usually, the freezing temperatures are between −50° C. and −80° C., however, one of skill in the art can determine the appropriate freezing temperature to lyophilize the reagent for use in the automated biochemical assay.

As used herein, the term "reconstituting" refers to the act of returning a lyophilized material to its liquid form. Thus, the term encompasses contacting a fluid, e.g., water or other suitable diluent, with a lyophilized reagent for sufficient time to allow the lyophilized reagent to absorb water, thereby forming a stabilized liquid reagent.

Receptacle & Cap

Accordingly, in an exemplary aspect, there is provided a receptacle 100 to receive and store fluid test samples for subsequent analysis, including analysis with nucleic acid-based assays or immunoassays diagnostic for a particular pathogenic organism. As shown in FIGS. 1A-1D, the receptacle 100 is a single-piece receptacle that includes a body 105 having a generally cylindrical upper portion 110 and a tapered lower portion 120. Formed on an outer surface of the body 105 is a laterally-extending flange, which, in the illustrated embodiment, comprises an annular ring 125, which separates the upper and lower portions of the body. The upper portion 110 of the body 105 has an open end 145 through which fluid samples are deposited or removed from the receptacle 100. The tapered lower portion 120 has a closed end 150 that may either be flat or rounded to provide optical communication with an optical system, for example, one or more optical fibers (not shown) of a biochemical analyzer. In various embodiments, the bottom surface of the closed-ended lower portion may be flat or curved.

The receptacle 100 optionally containing a sample or reaction mixture is configured for insertion into a receptacle holder of an automated biochemical analyzer (not shown). As used herein, a receptacle that is "configured for insertion" refers to the exterior surface of the body 105 of the receptacle 100 being sized and shaped to maximize contact between the receptacle and a receptacle well of a receptacle holder. In certain embodiments, this maximal contact refers to physical contact of the receptacle well with at least a portion of the receptacle 100. Also in certain embodiments, this maximal contact refers to physical contact of the receptacle well with the tapered lower portion 120 of the receptacle 100, or at least a portion the tapered lower portion 120 of the receptacle 100.

Formed in the inner surface 140 of the upper portion 110 of the body 105 is one or more longitudinally oriented grooves 135 to facilitate the venting of air displaced from the interior upon deposit of the test sample or attachment of a cap 200 to the receptacle 100. In various embodiments, a plurality (i.e., 2, 3, 4, 5, 6, 7, or 8) of longitudinally oriented grooves may be formed in the inner surface 140 of the upper portion 110, and the grooves 135 may be equally spaced apart from one another around the entire circumference of the body 105.

Circumscribing the open end 145 of the upper portion 110 of the body 105 is a lip 155 extending radially outward from a central axis thereof. In various embodiments, the lip 155 tapers from the outer-most portion of the radially-extended lip towards the open end of the body, and is configured for securable attachment to a cap 200 (FIGS. 2A-2D).

With reference now to FIGS. 2A-2D, the securable cap 200 includes a lower portion 220 having an outer surface for sealing engagement of the inner surface 140 of the upper portion 110 of the receptacle 100 and an upper portion 210. To ensure an essentially leak-proof seal when the cap 200 is securely attached to the open end 145 of the upper portion 110 of the receptacle 100, the outer surface of the lower portion 220 of the cap 200 is formed with one or more annular ribs 230 for contacting the inner surface 140 of the upper portion 110 thereof. In various embodiments, the lower portion 220 of the cap 200 is formed with 1, 2, or 3 annular ribs 230 for contacting the inner surface 140 of the upper portion 110 of the receptacle 100.

Figure 3A:
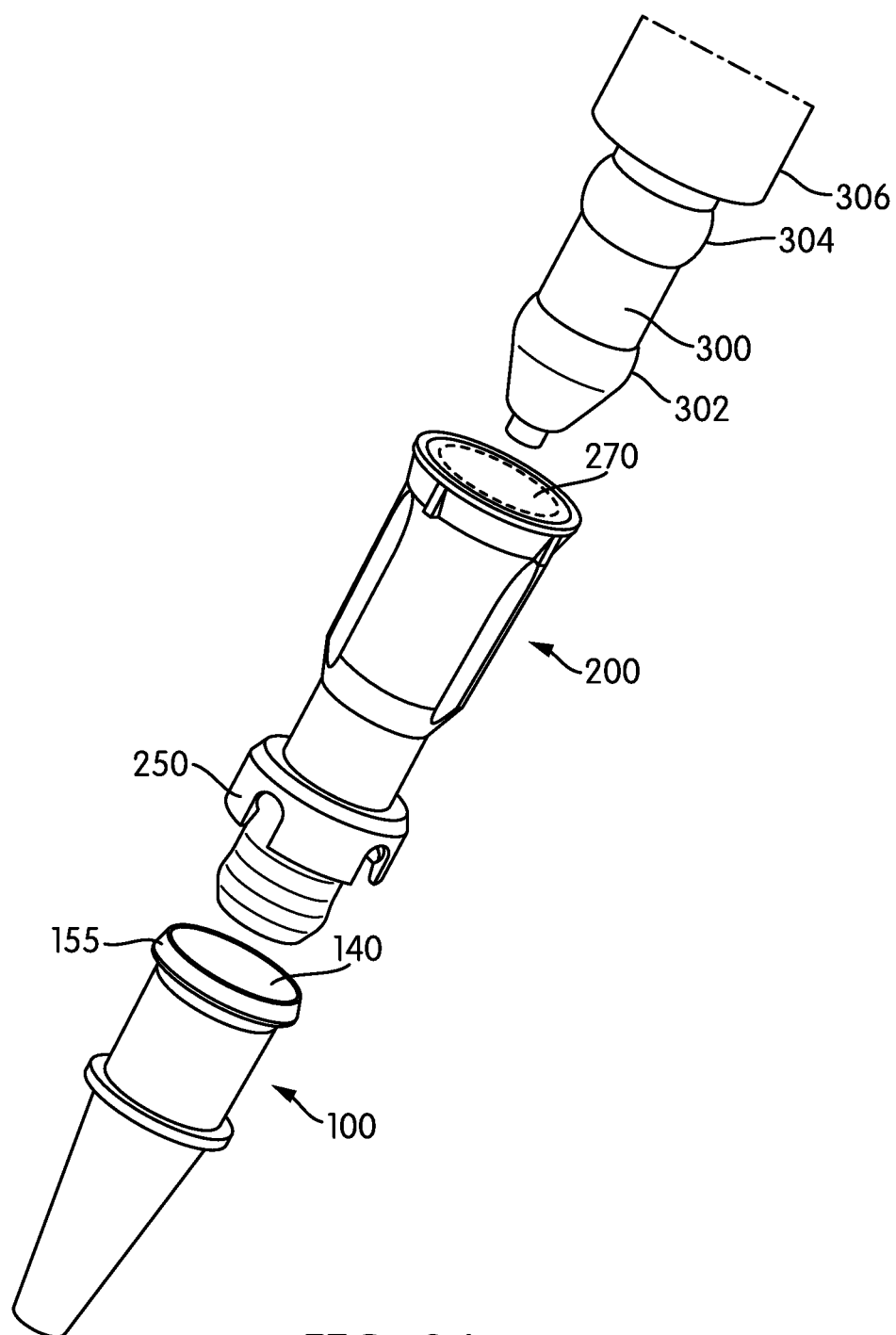
FIG. 3A is an exploded perspective view of the receptacle, the cap, and a portion of a receptacle transport mechanism configured to be inserted into the cap.

The upper portion 210 of the cap 200 includes an open end 215 for frictional attachment to a portion of a receptacle transport mechanism 300 (FIG. 3A), such as a tubular probe of a pipettor or pick-and-place robot. Guiding insertion of the receptacle transport mechanism 300 into the open end 215 of the upper portion 210 of the cap 200 are one or more linear ribs 260 formed in the inner surface 270 of the upper portion 210. The linear ribs 260 protrude towards an axial center of the cap 200, thereby decreasing the inner fitment diameter of the upper portion 210 of the cap 200. Each linear rib 260 may be beveled (as at 262) at an upper, or proximal, end thereof. These linear ribs 260 can, among other things, enhance the frictional attachment to the receptacle transport mechanism 300. In various embodiments, 1, 2, 3, 4, 5, 6, 7, or 8 linear ribs 260 are formed in the inner surface 270 of the cap 200 and extend at least a portion of the way down the length of the upper portion 210 thereof.

At least one of the linear ribs 260 may be formed with a portion 265 thereof, e.g., at a lower, or distal, end, that gradually tapers radially inward toward a central axis of the upper portion 210 of the cap. In other words, the amount of protrusion of the linear rib 260 may gradually increase in size as the linear rib 260 approaches the bottom 245 of the upper portion 210 of the cap 200. Alternatively, or in addition thereto, in certain embodiments, the linear rib 260 may gradually increase in overall thickness as it approaches the bottom 245 of the upper portion 210 of the cap 200. Thus, gradual increase in thickness or radial geometry is contemplated for the gradual tapering of the one or more linear ribs 260, which serves to stabilize and center the receptacle transport mechanism 300 as it is lowered into the cap 200 for transport.

Corresponding with each linear rib 260 and disposed on the exterior surface of the upper portion 210 of the cap 200 are one or more indentations, or recesses, 234 that extend along at least part of the length thereof. The recesses may be formed in any shape such as, for example, concave, notched, squared, etc. Thus, at least one recess 234 is formed in the exterior surface of the upper portion 210 of the cap 200. In various embodiments, the length of the recess 234 is the same as the length of the corresponding linear rib 260, and each linear rib 260 is positioned such that it lies on the inner surface 270 of the cap 200 in a location that directly opposes the position of the at least one recess 234 formed on the outer surface of the cap 200 in a one-to-one relationship. The coupling of a linear rib 260 with an recess 234 in this manner enhances the predictability of the frictional attachment of the cap 200 to a receptacle transport mechanism 300. In certain embodiments, as the receptacle transport mechanism 300 is lowered into the open end 215 of the cap 200, it contacts the one or more linear ribs 260, thereby pressing against the one or more linear ribs 260. Such pressing against the linear ribs 260 causes the cap 200, and recesses 234 to flex and/or expand radially outward with respect to the axial center thereof to accommodate the receptacle transport mechanism 300 and thus enhance frictional attachment of the cap 300 to the receptacle transport mechanism 300. Accordingly, 1, 2, 3, 4, 5, 6, 7, or 8 recesses 234 may be formed on the exterior surface of the upper portion 210 of the cap 200.

Circumscribing the open end 215 of the upper portion 210 of the cap 200 is a lip 225 extending radially outward from a central axis thereof. In various embodiments, the lip 225 tapers from the open end 215 towards the lower portion 220. Protruding from the taper of the lip 225 are a plurality of protrusions 235. The protrusions 235 may be equally spaced apart from one another and facilitate stacking and/or docking within a well of a multi-well tray 400 (FIG. 4A) for use in an automated biochemical analyzer. In various embodiments, 1, 2, 3, 4, 5, 6, 7, or 8 protrusions 235 are formed in the taper of the lip 225.

In various embodiments, the cap 200 is removed from the receptacle transport mechanism 300 by means of a sleeve 306 coaxially disposed over a tip of the receptacle transport mechanism 300 and axially movable with respect to thereto. The sleeve 306 moves axially with respect to the tip toward a distal end of the tip and contacts the lip 225 of the cap, thereby pushing the cap off the tip of the receptacle transport mechanism 300.

Separating the upper portion 210 from the lower portion 220 of the cap 200 is a flange 240 that extends radially away from an axial center thereof. The flange 240 includes a plurality of locking arms 250 that extend from the flange 240 toward the lower portion 220 of the cap 200. The locking arms 250 are shaped for securely engaging the lip 155 of the receptacle 100, and may be disposed to allow for removable attachment of the cap 200 to the receptacle 100, while maintaining a leak-proof seal of the contents thereof. In various embodiments, 1, 2, 3, 4, 5, 6, 7, or 8 locking arms 250 are formed in the cap 200.

The flange 240 of the cap 200 additionally serves to form a bottom 245 to separate the upper portion 210 from the lower portion 220, thereby closing the interior of the receptacle 100 from the environment. However, in certain embodiments, the bottom 245 is scored 255 for piercing by a mechanism for collecting and/or adding reagents to the test sample within the receptacle 100. Such piercing avoids the need to remove the secured cap 200 from engagement with the receptacle 100, while providing access to the contents therein.

The receptacle 100 and cap 200 of the present disclosure may be prepared from a number of different polymer and heteropolymer resins, including, but not limited to, polyolefins (e.g., high density polyethylene ("HDPE"), low density polyethylene ("LDPE"), a mixture of HDPE and LDPE, or polypropylene), polystyrene, high impact polystyrene and polycarbonate. An example of an HDPE is sold under the trade name Alathon M5370 and is available from Polymerland of Huntsville, N.C.; an example of an LDPE is sold under the trade name 722 and is available from The Dow Chemical Company of Midland, Mich.; and an example of a polypropylene is sold under the trade name Rexene 13T10ACS279 and is available from the Huntsman Corporation of Salt Lake City, Utah. Although LDPE is a softer, more malleable material than HDPE, the softness of LDPE provides flexibility in the locking arms 250 of the cap 200 to securably engage the lip 155 of the receptacle 100. And, while a cap made of HDPE is more rigid than one made of LDPE, this rigidity tends to make an HDPE cap more difficult to penetrate than one made of LDPE. It should be understood that the receptacle 100 and cap 200 may be comprised of a combination of resins, including, for example, a mixture of LDPE and HDPE, preferably in a mixture range of about 20% LDPE:80% HDPE to about 50% LDPE:50% HDPE by volume. In addition, the amounts of LDPE and HDPE used to form each of the receptacle 100 and cap 200 may be the same or different. In various embodiments, at least a portion of the cap 200 is formed from an opaque material having low to no autofluorescence characteristics. Also, in certain embodiments, the portion of the cap 200 formed from an opaque material having low to no autofluorescence characteristics is at least the lower portion 220 thereof, including the inner surface 232 of the lower portion 220 of the cap 200.

Regardless of the type or mixture of resins chosen, the receptacle 100 and cap 200 are preferably injection molded as unitary pieces using procedures well-known to those skilled in the art of injection molding, including a multi-gate process for facilitating uniform resin flow into the receptacle and cap cavities used to form the shapes thereof. Uniform resin flow is desirable for achieving consistency in thickness, which is important for a variety of reasons, including for the penetrable bottom 245 of the cap 200; to ensure a secure, such as an air-tight, engagement of the cap 200 and receptacle 100; to ensure a predictable engagement of the cap 200 with the receptacle transport mechanism 300; and to ensure maximal contact of the receptacle 100 with a receptacle well of a receptacle holder.

Method for Automated Removal of a Cap

Figure 3B:
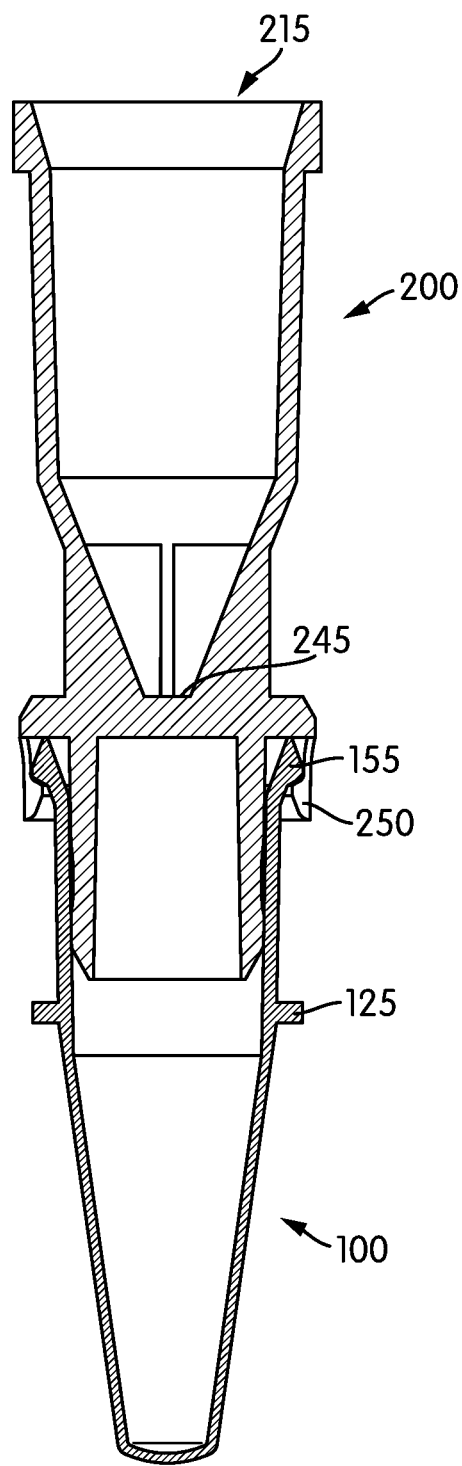
FIG. 3B is a side cross-sectional view of the cap installed in the receptacle.

In another aspect, disclosed herein is a method for automated removal of a cap from a capped reaction receptacle. The method includes providing a receptacle 100 securably engaging the lip 155 of a receptacle 100, as shown in FIG. 3B. Thereafter, performing an automated motion of contacting an inner portion 280 of at least one of the plurality of locking arms 250 of the cap 200 with a raised annular ridge defined around a receptacle slot. The receptacle slot may be provided in a receptacle holder of an automated biochemical analyzer, alternatively the receptacle slot may be provided in a card or cartridge intended to be removed from an automated biochemical analyzer. The contacting urges the locking arms 250 away from the lip 155 of the receptacle 100, thereby disengaging the cap 200 from the receptacle 100. While the cap 200 is being disengaged from the receptacle 100, an automated motion is performed to lift the cap 200 away from the receptacle 100, thereby removing the cap 200 from the receptacle 100. In various embodiments, the automated motion is performed by a receptacle transport mechanism 300 (FIG. 3A), such as, for example, a pipettor or pick-and-place robot.

Multi-Well Tray

Figure 4A:
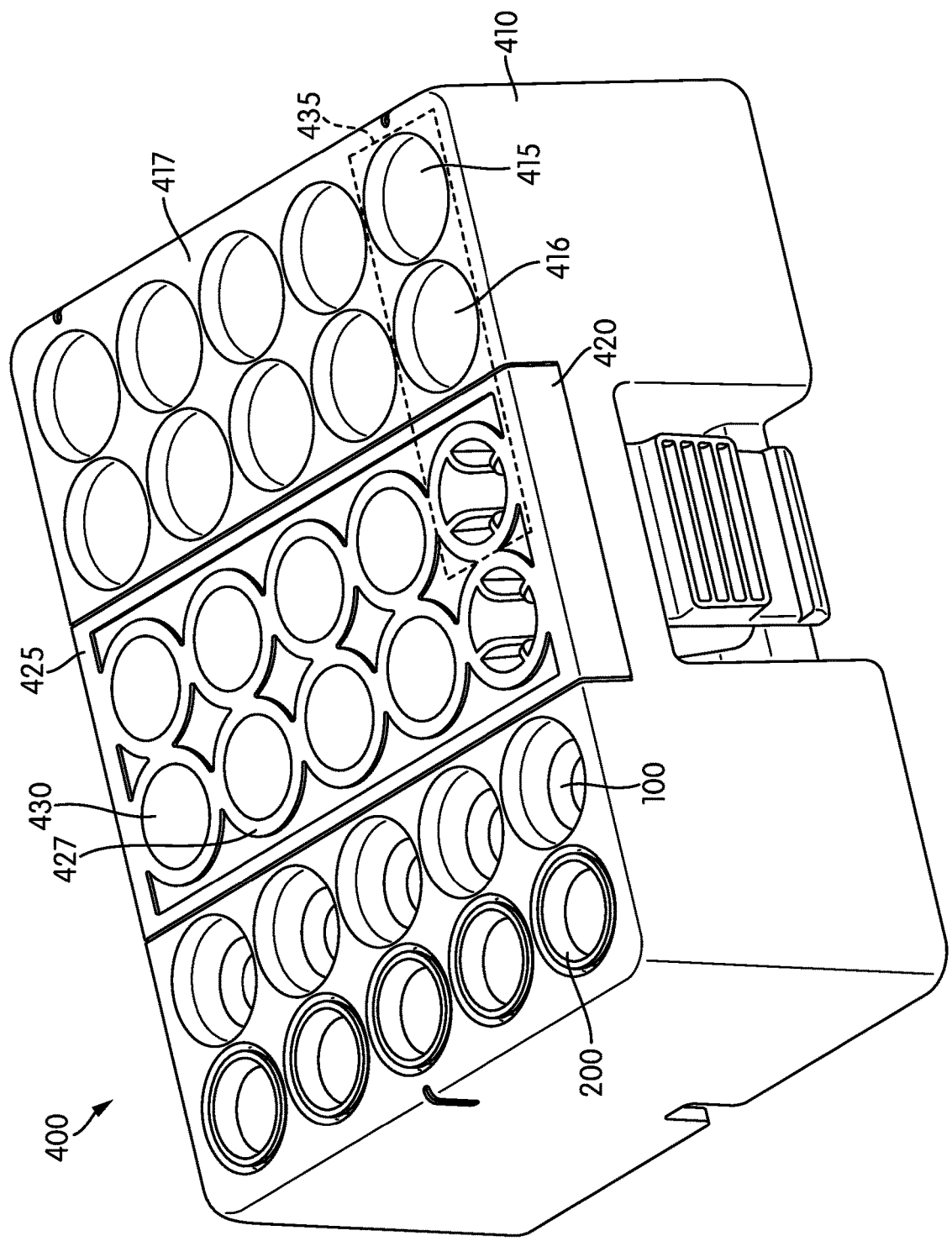
FIG. 4A is a perspective view of a multi-well tray for use in an automated reagent-based analyzer.
Figure 4B:
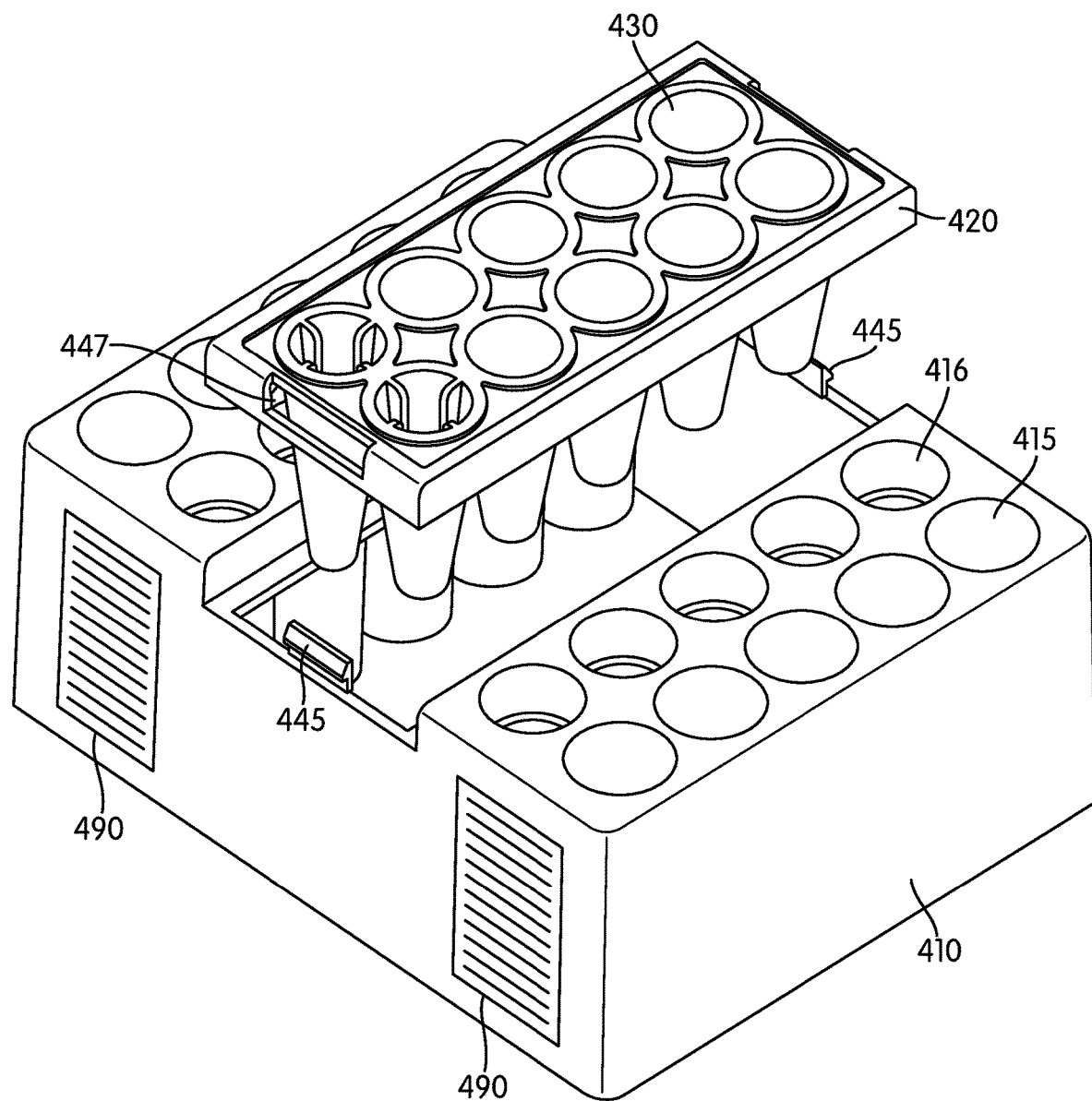
FIG. 4B is a perspective view of the multi-well tray with a card insert exploded from the multi-well tray.
Figure 5A:
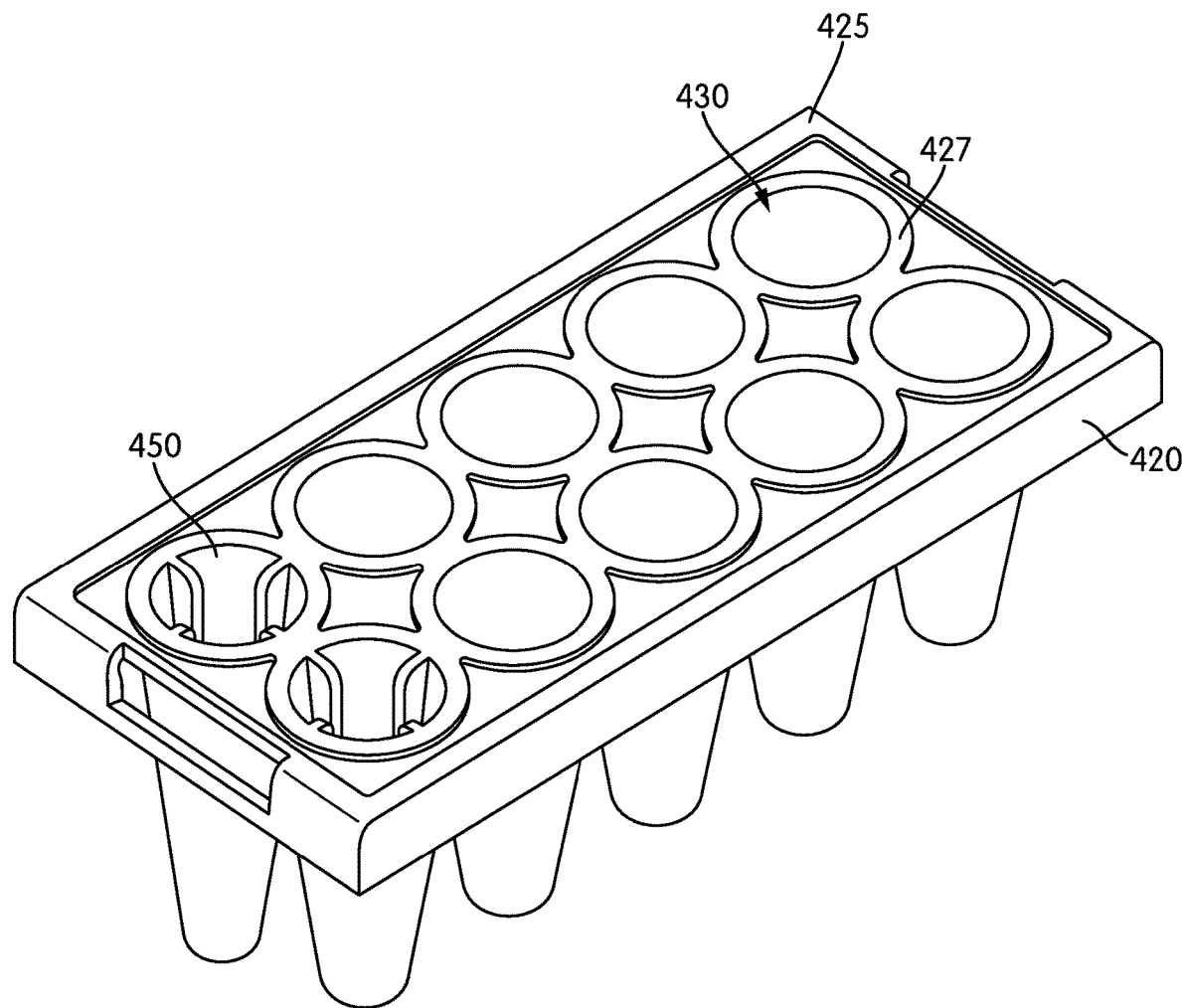
FIGS. 5A-5E are pictorial diagrams showing details of a card insert.

In another aspect, disclosed herein is a multi-well tray for use in an automated process. Referring now to FIGS. 4A and 4B, a multi-well tray 400, as shown, includes a base 410 having disposed in a top surface 417 thereof, a plurality of wells 415, 416. A card insert 420 (see also FIG. 5A) configured for removable attachment to the base 410, is attached thereto. When the card insert 420 is attached to the base 410, a top surface 425 of the card insert 420 is substantially parallel to and flush with the top surface 417 of the base 410.

Disposed in the top surface 425 of the card insert 420, is a plurality of wells 430, each configured for containing one or more reagents used for performing a biochemical analysis. Each well 430 of the card insert 420 corresponds to at least one of the wells 415 disposed in the base 410. Thus, in certain embodiments, after attachment of the card insert 420 to the base 410, the multi-well tray 400 takes on the uniform appearance of, for example, a multi-well plate. The wells 415, 416 disposed in the base 410 may be arranged in pairs, where each pair corresponds to a single well 430 of the card insert 420. As such, the multi-well tray 400 may include a plurality of sets 435 of wells, where each set 435 includes a first well 415 and a second well 416, which are disposed in the top surface 417 of the base 410, and a third well 430 disposed in the top surface 425 of the card insert 420. The wells of each set 435 of wells may be in alignment with each other, thereby resulting in a multi-well tray 400 that is spatially indexed such than an automated receptacle transport mechanism 300 can accurately identify and/or access any of the plurality of wells when the multi-well tray 400 is placed or inserted into an automated system. In certain embodiments, the multi-well tray 400 includes ten sets 435 of wells. As such, the base 410 is formed with ten pairs of first and second wells 415, 416 and the card insert 420 is formed with ten third wells 430, where each of the first, second, and third wells of the set 435 are arranged in alignment with each other. Thus, the multi-well tray 400 may include ten receptacles 100 and ten caps 200 provided therein for used in an automated biochemical analyzer.

The first and second wells 415, 416 of the set 435 are configured to receive a cap 200 and a receptacle 100, respectively. While it should be understood that the terms "first" and "second" as used to distinguish the wells formed in the base 410, for descriptive purposes, the "first well", or cap well, 415 will refer to a well configured to receive a receptacle cap 200.

Figure 7A:
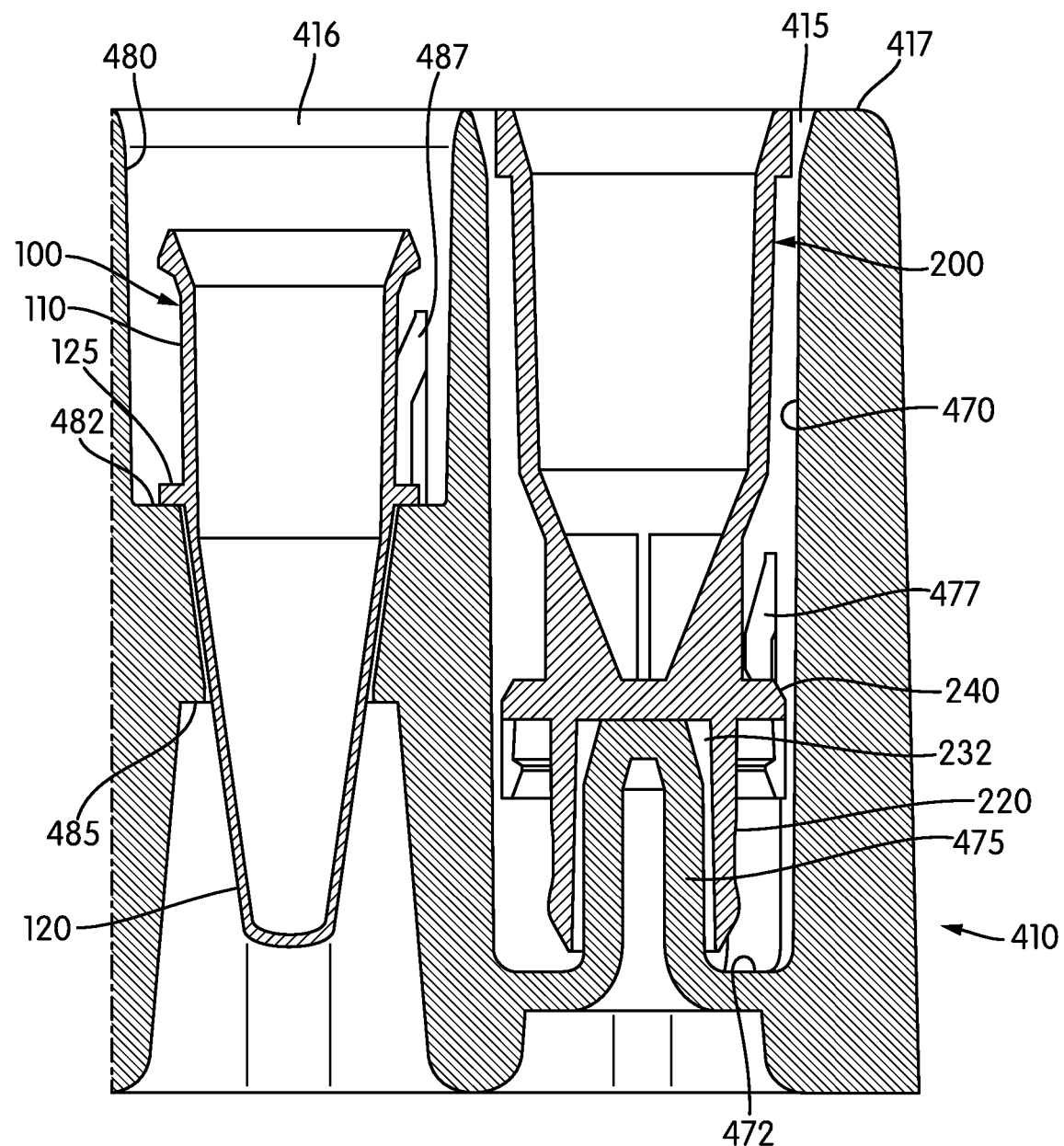
FIGS. 7A and 7B are cross-sectional views showing a cap and receptacle contained within the wells of the multi-well tray.
Figure 7B:
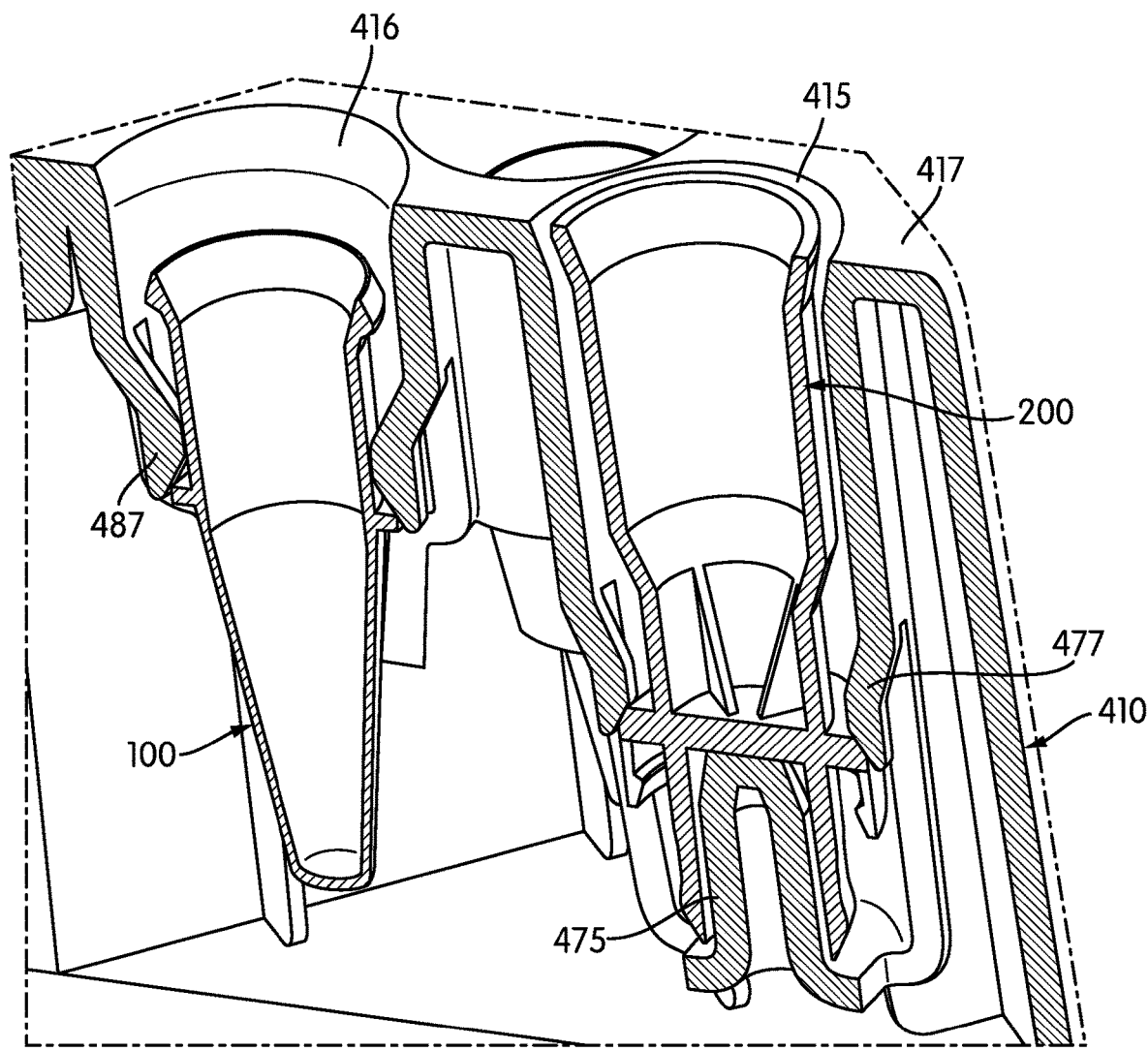

With reference now to FIGS. 7A and 7B, the first well 415 of the base 410 is defined by a cylindrical wall 470 and a bottom wall 472. Formed in the center of the bottom surface 472 is a protrusion 475 extending upwardly toward the top surface 417 of the base 410. The protrusion 475 is sized and shaped for engagement, optionally frictional engagement, with a hollow portion 232 of the lower portion 220 of the cap 200. Alternatively, or in addition thereto, the cylindrical wall 470 may be formed with a plurality of tabs 477 protruding towards the axial center of the first well 415. Such tabs 477 are configured for securely engaging at least a portion of the cap 200 to prevent the cap 200 from dislodging from the multi-well tray if, for example, the multi-well tray is inverted or shaken. In certain embodiments, 2, 3, 4, 5, 6, 7, or 8 tabs 477 are formed in the cylindrical wall 470 of the first well. Each of tabs 477 may securely engage the top surface of the flange 240 of the cap 200.

Similarly, the "second well", or receptacle well, 416 will refer to a well configured to receive a receptacle 100. As shown in FIGS. 7A and 7B, the second well 416 is defined by a cylindrical wall 480 and a bottom wall 482. Formed in the center of the bottom wall 482 is a through-hole 485 base. The through-hole 485 is sized and shaped in conformance with the outer surface of the lower portion 120 of the receptacle 100. As such, the through-hole may be tapered at an angle corresponding to the angle of the lower portion 120. As shown in FIG. 7A, the bottom wall 482 of the second well 416 forms an annular ledge at the perimeter of the through-hole for engaging the ring 125 of the receptacle 100. Alternatively, or in addition thereto, the cylindrical wall 480 may be formed with a plurality of legs 487 protruding towards the axial center of the second well 416. Such legs 487 are configured for securely engaging at least a portion of the receptacle 100 to prevent the receptacle 100 from dislodging from the multi-well tray if, for example, the multi-well tray is inverted or shaken. In certain embodiments, 2, 3, 4, 5, 6, 7, or 8 legs 487 are formed in the cylindrical wall 480 of the second well 416. Each of the legs 487 may securely engage the top surface of the ring 125 of the receptacle 100.

Figure 8:
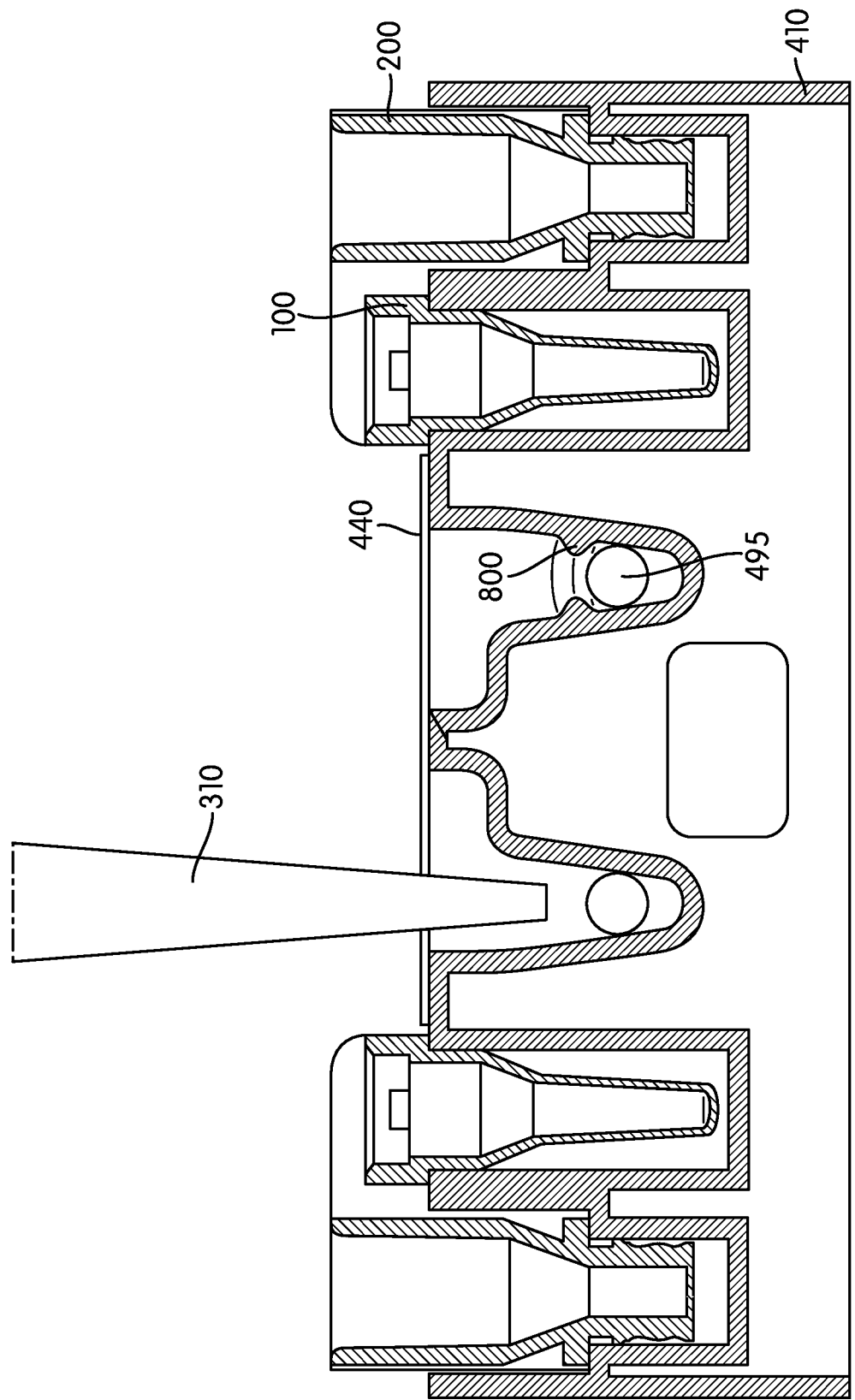
FIG. 8 is a pictorial diagram showing a cross-sectional view of an automated pipettor reconstituting a lyophilized reagent contained in a well of a multi-well tray.

As discussed above, the third well, or reagent well, 430 of each set 435 contains one or more reagents for performing a biochemical analysis. In certain embodiments, the third well 430 of the set 435 contains a lyophilized reagent 495 (FIGS. 8 and 9C), and may be sealed with a frangible seal 440 (FIG. 8). For example, each well 430 of the card insert 420 may be sealed with a metallic foil (or foil laminate) using, for example, a pressure sensitive adhesive which is applied to the top surface 425 thereof. The frangible seal 440 may further include a plastic liner, such as a thin veneer of HDPE applied to one or both surfaces thereof, which promotes attachment of the frangible seal 440 to the top surface 425 when a heat sealer is used. Heat sealing is a well-known process and involves the generation of heat and the application of pressure to the surface being sealed, which, in this case, is the top surface 425 or a raised lip 427 (see FIGS. 4A, 5A) surrounding the well 430 of the card insert 420. Alternatively, any known ultrasonic welding procedure using either high frequency or high amplitude sound waves may also be used to affix the frangible seal 440 to the card insert 420. The card insert 420 may include a plurality of frangible seals 440, each of which sealing a single well 430, or may include a single sheet that seals all wells 430 disposed therein.

A single lyophilized reagent 495 may be provided in each well 430 of the card insert 420. However, in certain embodiments, one or more wells 430 of the card insert 420 may contain a different lyophilized reagent 495, such as a different target-specific reagent. Thus, each well 430 of the card insert 420 may contain a distinct lyophilized reagent 495 compared with the lyophilized reagent 495 contained in at least one other of the plurality of wells 430 therein. In various embodiments, the card insert 420 does not contain non-reagent consumables. As used herein, a "reagent" refers to a substance or mixture for use in a chemical or biochemical reaction. Thus, a "non-reagent consumable" refers to a component that is used by an automated biochemical assay, but is not a reagent. Exemplary non-reagent consumables include, but are not limited to, contamination limiting elements, receptacles 100, and caps 200.

Figure 5B:
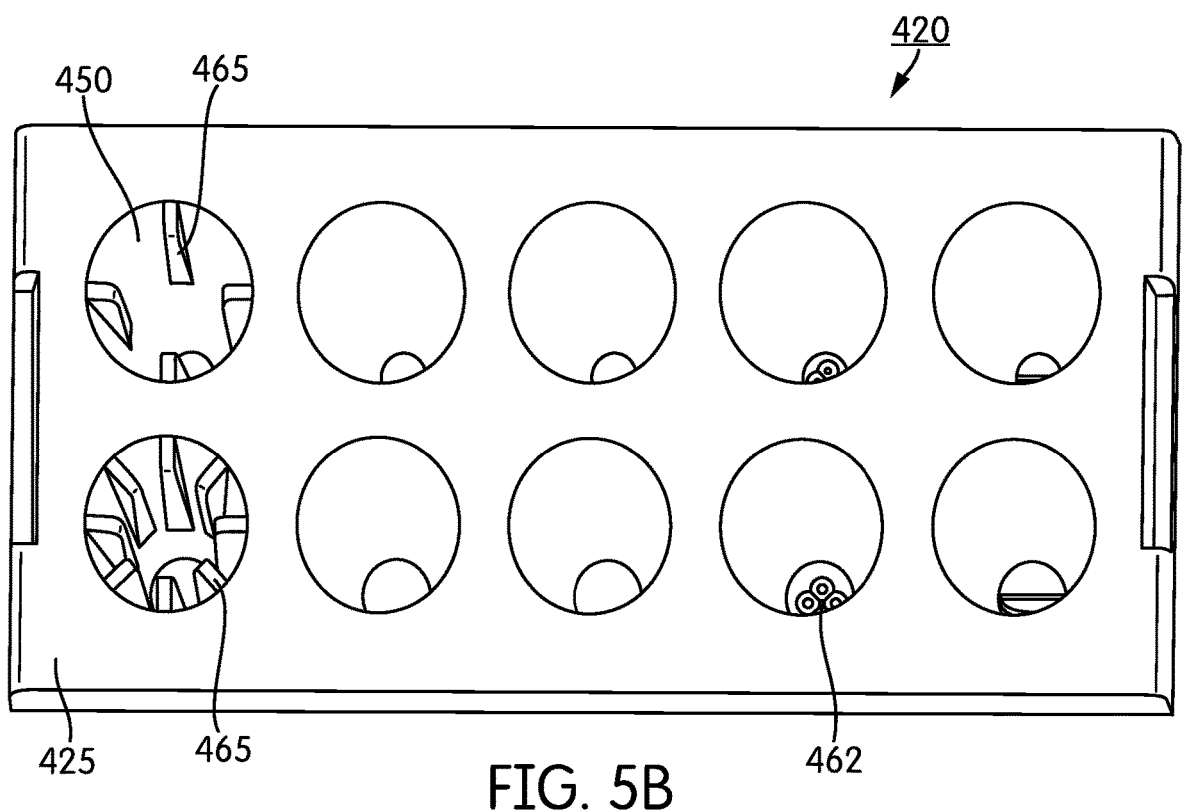
Figure 5C:
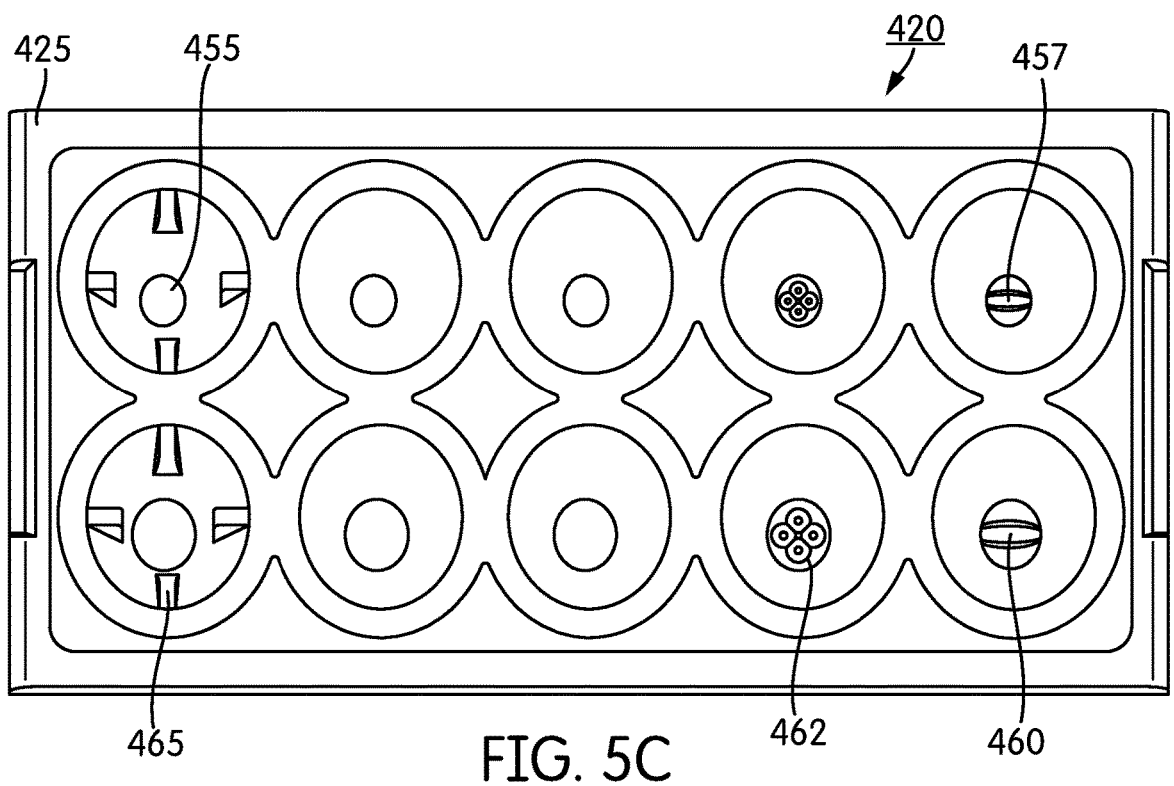
Figure 5D:
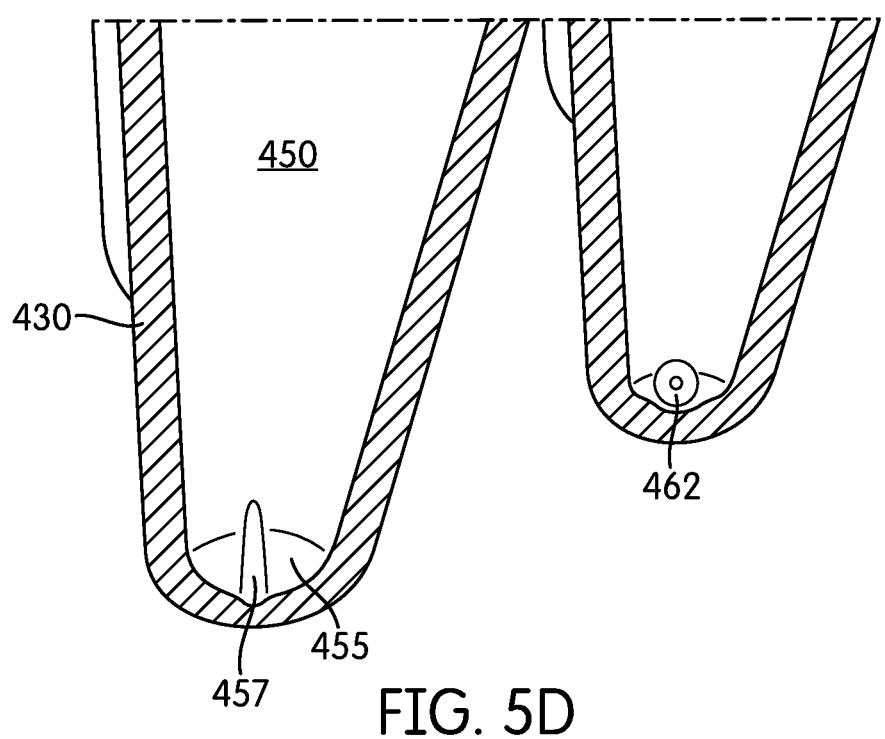

Referring now to FIGS. 5A-5E, each well 430 of the card insert 420 is defined by a side wall, or well wall, 450 and a bottom, or bottom wall or bottom wall portion, 455. In various embodiments, the side wall 450 tapers from an upper end thereof to the bottom 455, and may therefore be referred to as a conical wall. As shown in FIGS. 5B-5E, the bottom 455 of each well may be formed with one or more features to facilitate deposit of and collection of fluid from the well. Such features include, but are not limited to a concave groove 457, 460 (FIGS. 5C, 5D, 5E), convex ridge (not shown), or a set of grooves positioned in a crisscross pattern (not shown). The features may be located at the axial center of the well 430, as shown in FIG. 5C, or may be off-set to a side thereof, as shown in FIG. 5B. Alternatively, or in addition thereto, the side wall 450 may be formed with a plurality of bumps 462 on the surface thereof for additional facilitation of depositing and/or collecting fluids contained therein. The side wall 450 of each well 430 of the card insert 420 may further be formed with a plurality of rigid guides 465 that protrude radially from the side wall 450 towards the axial center of the well 430. Such rigid guides 465 guide a pipette tip 310 (FIGS. 8 and 9C) mounted on an automated pipettor toward the axial center of the well 430 as the tip is lowered therein, and may further serve to retain the lyophilized reagent at, or adjacent to, the bottom 455 of the well 430. In various embodiments, each well 430 may be independently formed with 2, 3, 4, 5, 6, 7, or 8 rigid guides 465 protruding from the respective tapered side wall 450.

Figure 5E:
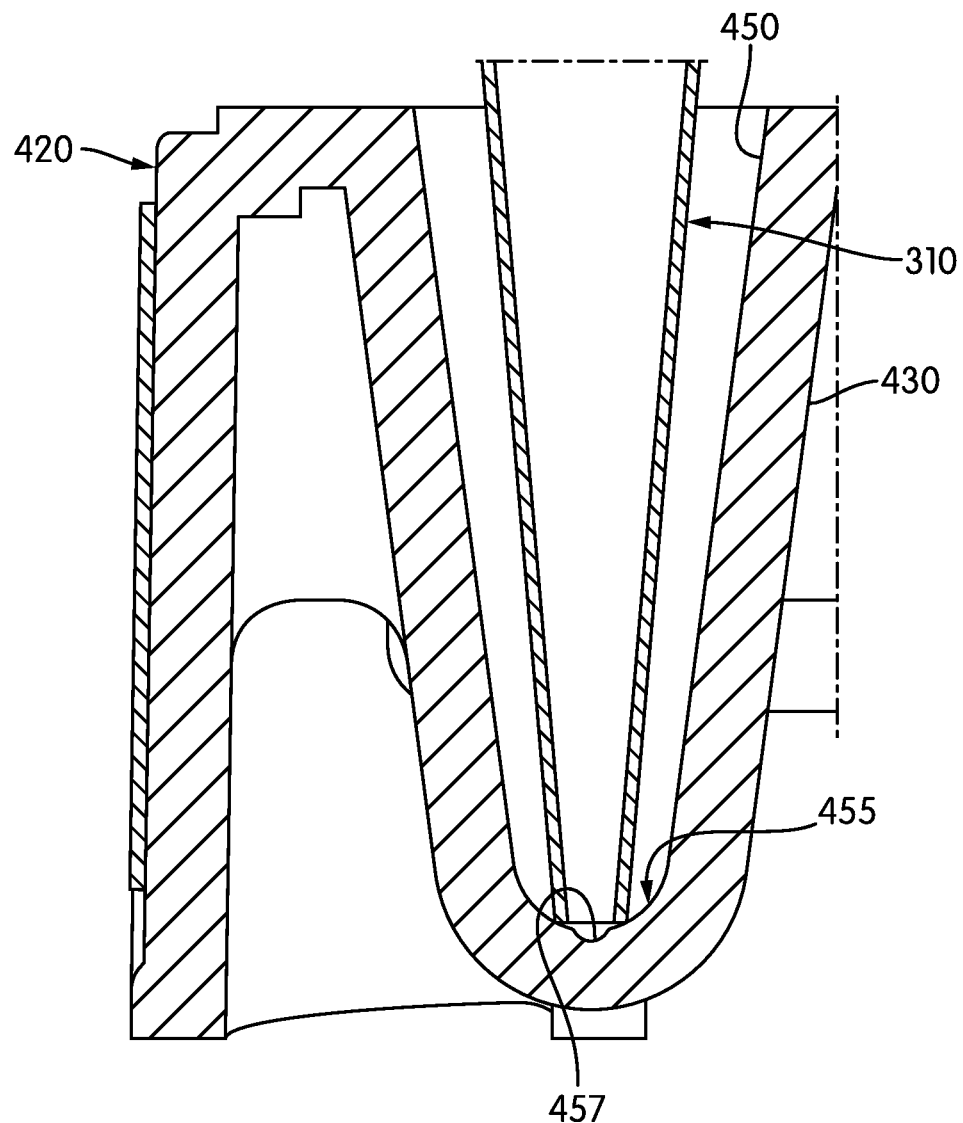

The features formed at the bottom 455 of the well 430, such as grooves, ridges, and/or bumps, interfere with the end of a pipette tip inserted into the well 430 and thus prevent the end of the pipette tip from making sealing contact with the bottom 455 so as to prevent a negative pressure build up within the pipette tip during a fluid aspiration. For example, as shown in FIG. 5E, a feature formed on the bottom 455 of well 430, such as groove 457, provides a clearance that prevents a pipette tip 310 from making sealing contact with the bottom 455 of the well 430.

Additionally, in certain embodiments, the side wall 450 of each well 430 of the card insert 420 may include one or more retention features (FIGS. 8, and 9C-9D) that can be used to retain the lyophilized reagent 495 at, or adjacent to, the bottom 455 of the well 430 when, for example a diluent is deposited into the well 430 for reconstitution of a lyophilized reagent. In FIGS. 9C and 9D, the retention features are shown within a well 715 of an alternative embodiment of a multi-well tray 700 described below. In various embodiments, the retention feature may include one or more protrusions or an annular ridge 800 formed above the area to be occupied by the lyophilized reagent 495, and extending toward the axial center of the well 430. Such protrusions or annular ridge 800 narrow the opening of the side wall 450 such that the opening is smaller than the diameter of the lyophilized reagent 495.

Figure 9A:
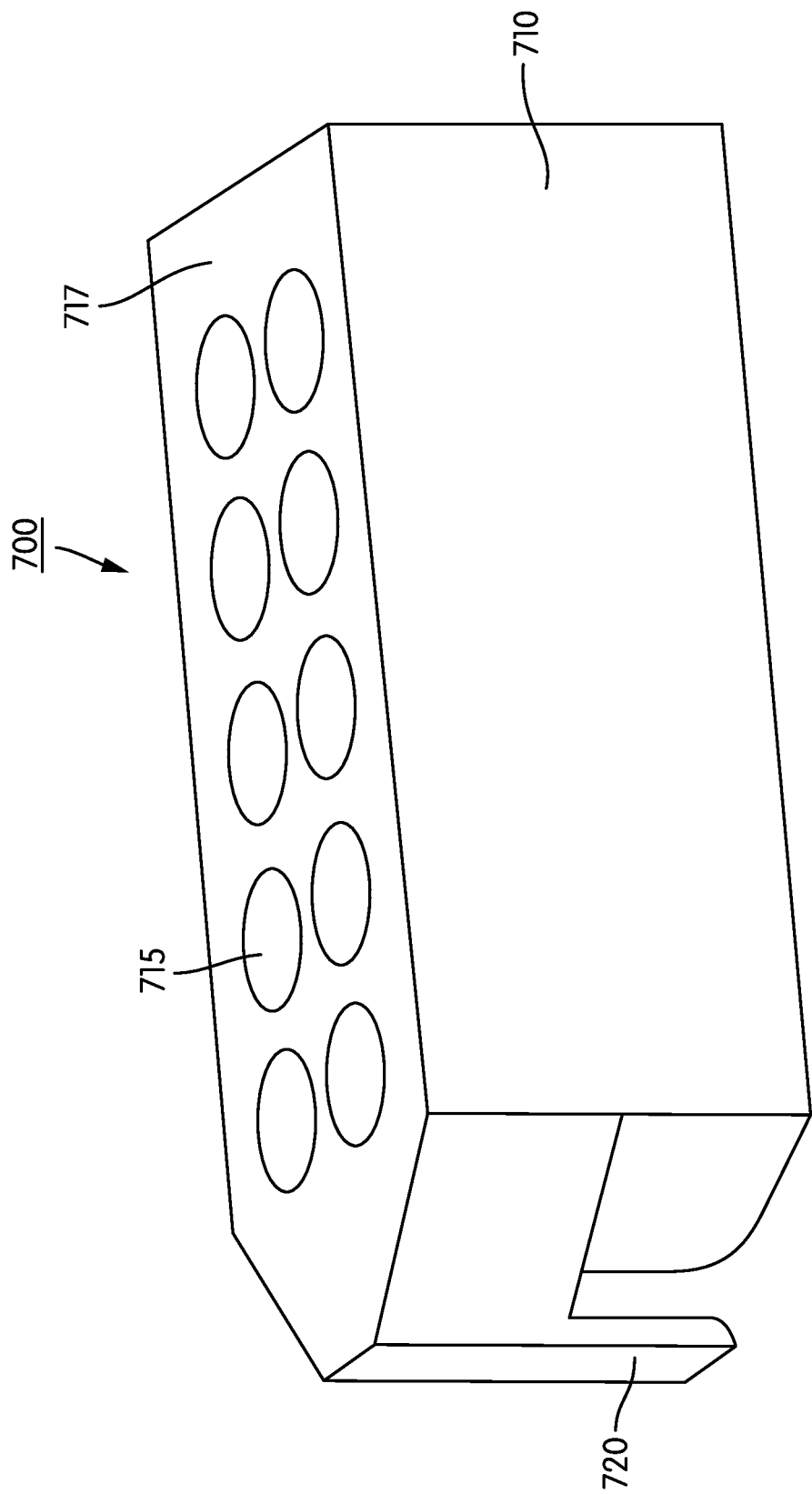
Figure 9B:
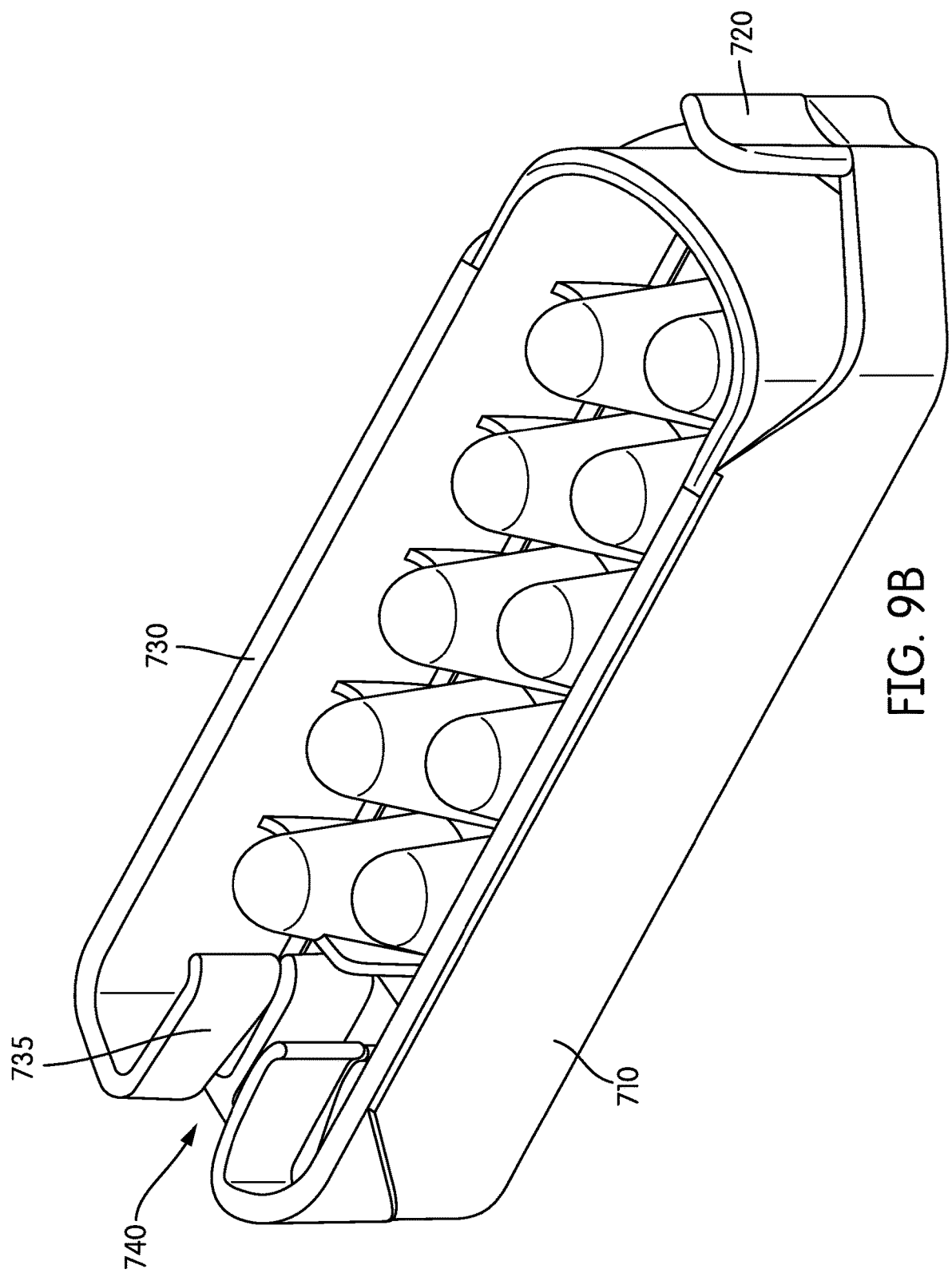
Figure 9D:
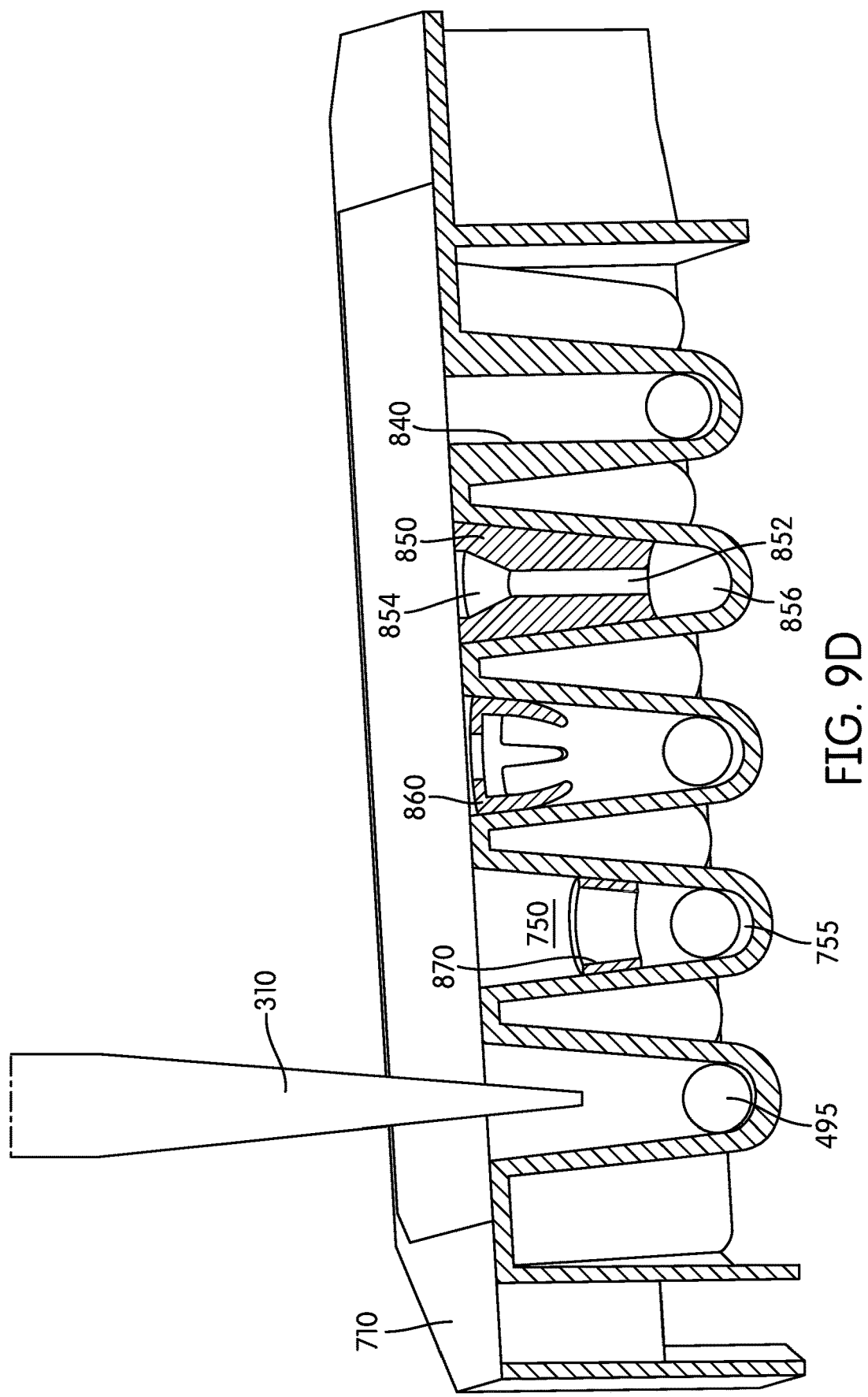
Figure 9E:
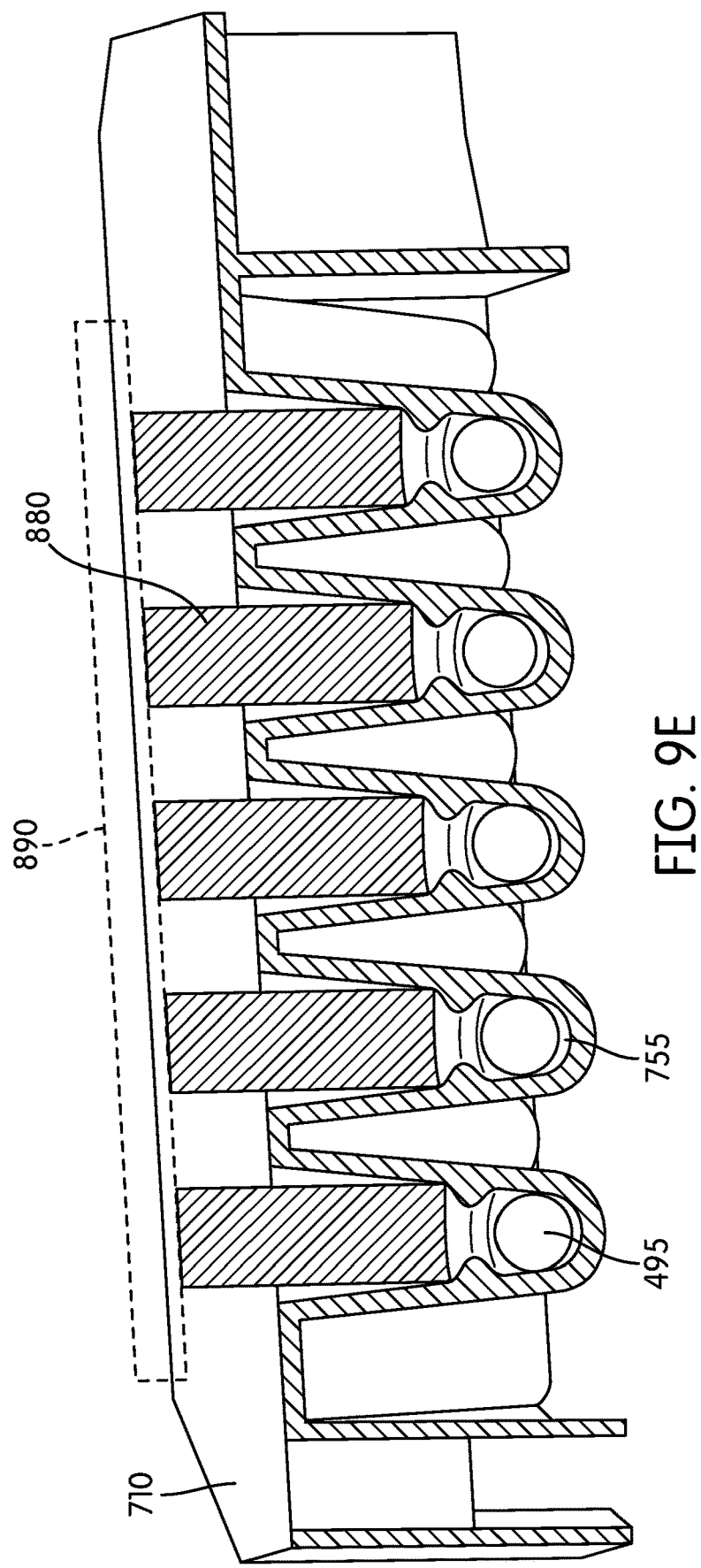

As shown in FIG. 9E, the annular ridge 800 may be formed by inserting one or more heat stakes 880 into the wells 430, such that the side wall 450 is deformed, thereby forming an annular ridge 800 therein. The one or more heat stakes 880 may be attached to an apparatus 890, which may heat the one or more heat stakes 880, thereby providing sufficient heat to deform the side wall 450 at a point along the taper where the diameter thereof equals that of the diameter of the heat stake.

In various embodiments, the retention feature may also take the form of one or more solid extensions 810 formed over the area to be occupied by the lyophilized reagent 495. Such extensions 810 connect opposing areas of the side wall 450, thereby retaining the lyophilized reagent 495 at, or adjacent to, the bottom 455 of the well 430. In various embodiments, the side wall 450 may be formed to mimic the thread of a coarse screw as shown at 820. Such a threaded feature 820 may be formed during injection molding of the well 430, or may be formed by applying a heated screw portion to the well wall, thereby forming a spiral channel along a length thereof, through which fluid may run to the bottom 455 using gravitational force. In various embodiments, the retention feature may be provided in the form of a tapered ring insert 830 that is fixedly attached to the side wall 450 either before or after deposit of the lyophilized reagent 495. The tapered ring 830 may be formed of plastic and include an exterior surface that tapers in accordance with the taper of the side wall 450. When present, the tapered ring 830 narrows the opening of the well 430 such that the lyophilized reagent 495 is retained at, or adjacent to, the bottom 455 of the well 430.

Whether the lyophilized bead 495 is formed within the well from an initially liquid reagent or the solid bead is formed outside the well and then placed into the well may depend on whether the retention feature is an integral part of the well. If the retention feature is an integral part of the well, a solid bead could not be placed into the well below the retention feature and a liquid reagent must be dispensed into the bottom of the well and then lyophilized. If the retention feature is not an integral part of the well, a lyophilized bead could be placed into the well, and then the retention feature installed in the well over the lyophilized bead.

As shown in FIG. 9D, the inner surface of a well wall may be substantially vertical as at 840, while an exterior surface of the well retains its tapered shape. In certain embodiments, the inner surface of the well wall may be substantially vertical as at 840, while the exterior surface of the well is also substantially vertical (not shown). When present, the vertical wall 840 allows the entirety of a liquid reagent to be lyophilized to settle at the bottom 455 of the well, thereby ensuring reagent uniformity upon lyophilization.

In various embodiments, as also shown in FIG. 9D, the retention feature may be in the form of a capillary insert 850 that is fixedly attached to the well wall. The capillary insert 850 may be formed of plastic and include an exterior surface that tapers in accordance with the taper of the well wall. In an exemplary embodiment, the well and capillary insert 850 may be formed as a single unit. The capillary insert 850 may not extend completely to the bottom of the well, thereby defining a chamber 856 below a bottom end of the capillary insert 850. The inner surface of the capillary insert 850 may include substantially vertical walls forming a capillary channel 852 extending from an upper end of the insert to a lower end of the insert through which fluid will flow via capillary attraction, and within which the fluid will be retained as a result of the combination of surface tension and adhesive forces between the fluid and the walls of the capillary channel. The capillary insert 850 may further include an open upper end 854 that tapers from a top surface of the insert 850 to the channel 852. Thus, when a capillary insert 850 is present in a well and a liquid reagent to be lyophilized is deposit therein, the reagent remains held within the capillary channel thereof, and is prevented from flowing into the bottom of the well. After lyophilizing the liquid reagent, the lyophilized reagent 495 remains lodged within the channel 852 of the capillary insert 850. Deposit of a diluent for reconstitution of the lyophilized reagent 495 is accomplished by addition of the diluent to the tapered open upper end 854 of the capillary insert 850. The diluent then flows within the capillary channel 852 via capillary attraction, and is retained therein as a result of the combination of surface tension and adhesive forces between the diluent and the walls of the capillary channel 852. Once reconstituted, the reagent may be collected by insertion of the pipette tip 310 into the tapered open upper end 854 of the capillary insert 850 and withdrawing the liquid reagent therefrom. The entirety of the liquid reagent may therefore be collected at the tapered open upper end 854 of the capillary insert 850 since the liquid will travel upwards due to capillary attraction within the channel 852 of the capillary insert 850.

Alternatively, or in addition thereto, the bottom 455 of the well can be formed to include a roughened surface, thereby providing sufficient surface area to which the lyophilized reagent 495 will adhere upon formation thereof. Alternatively, or in addition thereto, the lyophilized reagent 495 will adhere to, or adjacent to, the bottom 455 of the well 430 through a static electrical attractive force created on the well wall 450 and/or bottom 455 of the well 430. In such embodiments, the inner surface of the well 430 is provided with an electrical charge such that the lyophilized reagent 495 adheres thereto.

In various embodiments, the retention feature may take the form of an insert through which the pipette tip 310 may be inserted. For example, as shown in FIG. 9D the retention feature may be a fingered collar 860 that is fixedly attached to a top portion of the well. The fingered collar 860 may be formed of plastic and include an exterior surface that tapers in accordance with the taper of the well wall. The fingered collar 860 may include one or more (i.e., 1, 2, 3, 4, 5, 6, 7, or 8) fingers extending from a bottom surface thereof, and protruding along a radius of curvature toward the axial center of the well. The one or more fingers may be flexible such that contact with a pipette tip 310 inserted therein causes the fingers to flex toward the well wall, thereby allowing the pipette tip 310 to pass there through. Upon withdrawal of the pipette tip 310, the fingers return to a rest position such that the fingers protrude along the radius of curvature toward the axial center of the well.

In an alternative embodiment, the retention feature may take the form of a collar 870 that resembles the fingered collar 860, but does not include the one or more fingers protruding therefrom. Such a collar 870 may be fixedly attached to a top or center portion of the well wall, and may be formed of plastic and include an exterior surface that tapers in conformance with the taper of the well wall. When present, the collar 870 narrows the well wall to retain the lyophilized reagent 495 at, or adjacent to, the bottom 455 of the well, while allowing the pipette tip 310 to pass there through.

Each of the base 410 and card insert 420 may be independently constructed of an injection molded plastic, such as the plastics described above. The plastic used to form the base 410 may be the same or different from the plastic used to form the card insert 420. For example, the card insert 420 may be formed from a plastic having lower permeability to air and/or moisture than the plastic forming the base 410. Such plastics may be more expensive than their conventional counterparts but, due to the decreased air and moisture permeability, provide for enhanced stability of reagents, such as lyophilized reagents contained in the wells thereof. Any exterior surface of the base 410 or card insert 420 may further include one or more identifying labels 490, such as a barcode, 2D barcode, quick response (QR) code, radio frequency identification (RFID), or other human or machine readable indicia, disposed thereon. The information carried on such label may include identifying information regarding the multi-well tray 400 and/or card insert 420, including information regarding the reagents contained therein, such as lot number, serial number, assay type, expiration date, etc. In various embodiments, the base 410 may include one or more barcodes and/or QR codes on a side surface thereof for identifying assays to be performed by the automated biochemical analyzer.

As shown in FIG. 4B, the base 410 may be formed with one or more locking arms 445 positioned for locking engagement with the card insert 420. Additionally, the card insert 420 may be formed with one or more corresponding lock-holes 447 for receiving the locking arms 445 of the base 410. Once secured into the base 410 by the locking arms 445 and/or the lock-holes 447, the card insert 420 is prevented from detachment therefrom. However, in certain embodiments, locking arms 445 may be moved out of locking engagement with the card insert 420 to release the card insert 420 from the base 410. Such releasable engagement provides for reuse of the base 410, if necessary, and/or replacement of a card insert 420 should the need arise.

Figure 6A:
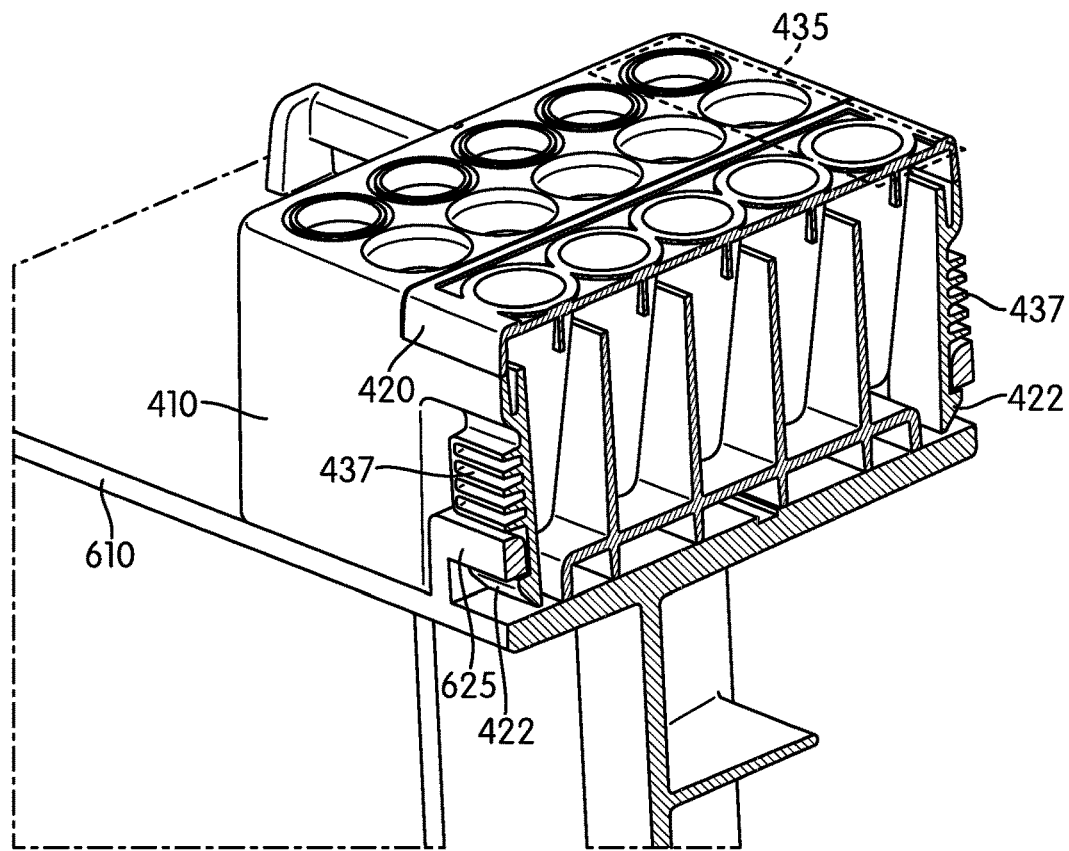
FIGS. 6A and 6B are pictorial diagrams showing attachment of the card insert to the base of the multi-well tray.

As shown in FIG. 6A, base 410 may be further formed with one or more locking fingers 422 disposed on a side surface thereof. The locking fingers 422 are configured for releasably engaging a rack to secure the base 410 to the rack for use in automated processing. In various embodiments, the base 410 may further include a release 437 for urging the locking fingers 422 away from the engaging surface of the rack to facilitate removal therefrom.

Figure 6B:
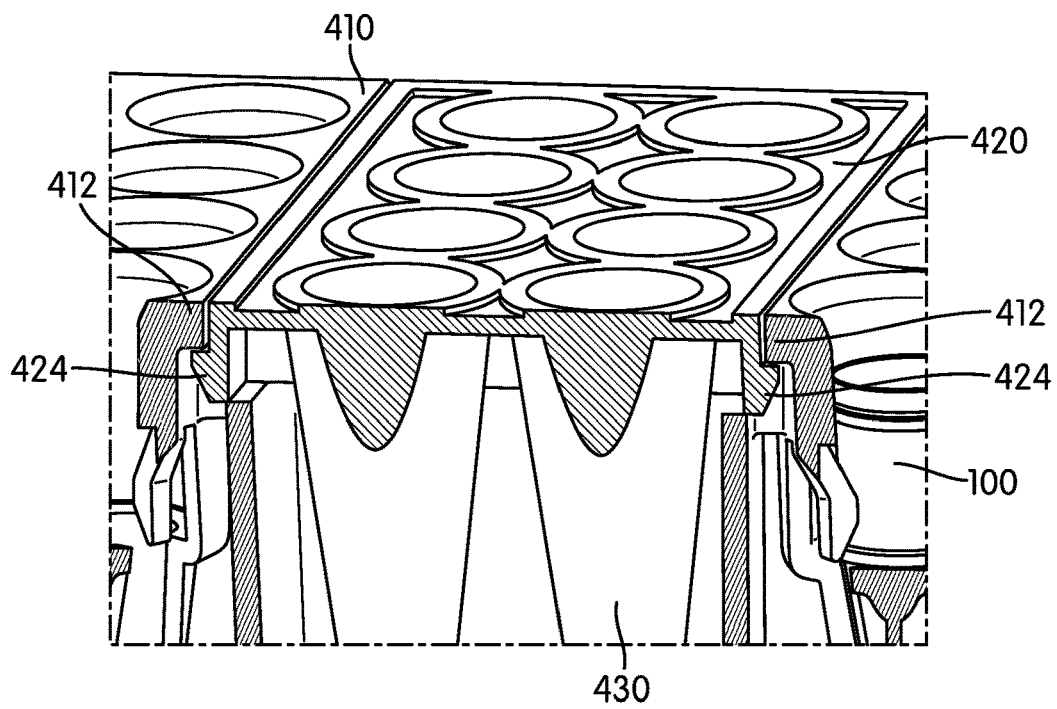

As shown in FIG. 6B, the card insert 420 may be secured to the base 410 by means of locking features 424 disposed along opposed sides of the card insert 420 that are configured for locking engagement with cooperating ledges 412 formed in the base 410.

FIGS. 9A-9E show an alternative embodiment of a multi-well tray 700. Referring now to FIGS. 9A and 9B, the multi-well tray 700 includes a base 710 having disposed in a top surface 717 thereof, a plurality of wells 715. The base 710 also includes an arm 720 for engagement by a transport mechanism, such as a rotary distributor (not shown) for transport within an automated biochemical analyzer. As shown in FIG. 9B, the bottom surface 730 of the base 710 is formed with one or more snap fingers 735, which define a slot 740 into which an element (not shown) of the biochemical analyzer is inserted. Thus, snap fingers 735 grasp the element (not shown) of the biochemical analyzer, thereby forming a secure attachment thereto.

In this alternative embodiment, all of the wells 715 are configured to contain one or more reagents used for performing automated biochemical analysis. Similar to the wells 430 of the multi-well tray insert 420, each well 715 is defined by an inner side wall 750 and a bottom 755. In various embodiments, the side wall 750 tapers from a top portion of the well 715 to the bottom 755, as shown in FIG. 9C.

As discussed above, the bottom 755 of each well 715 may be formed with one or more features to facilitate deposit of and collection of fluid from the well. Such features include, but not limited to a concave groove 457, 460 (FIGS. 5B-5D), a convex ridge (not shown), or a set of grooves positioned in a crisscross pattern (not shown). The features may be located at the axial center of the well 715, as shown in FIG. 5C, or may be off-set to a side thereof, as shown in FIG. 5B. Alternatively, or in addition thereto, the inner wall 750 may be formed with a plurality of bumps 462 (FIGS. 5B-5D) on the surface thereof for additional facilitation of depositing and/or collecting fluids contained therein. The inner wall 750 of each well 715 of the card 700 may further be formed with a plurality of rigid guides 465 (FIG. 5B) that protrude radially from the inner wall 750 towards the axial center of the well 715. Such rigid guides 465 guide the tip 310 (FIGS. 8 and 9C) mounted on an automated pipettor toward the axial center of the well 715 as the tip is lowered therein, and may further serve to retain the lyophilized reagent 495 at, or adjacent to, the bottom 755 of the well 715. In various embodiments, each well 715 may be independently formed with 2, 3, 4, 5, 6, 7, or 8 rigid guides protruding from the respective tapered well wall 750.

Additionally, in certain embodiments, the inner well walls 750 of each well 715 of the card 700 may include one or more retention features 800, 810, 820, 830, 840, 850, 860, 870 (FIGS. 8 and 9C-9D), as described above, configured to retain the lyophilized reagent 495 at, or adjacent to, the bottom 755 of the well 715 when, for example a diluent is deposited into the well 715 for reconstitution. In various embodiments, the retention features may include an annular ridge 800 formed above the area to be occupied by the lyophilized reagent 495, and extending toward the axial center of the well 715. In various embodiments, the retention features may also take the form of one or more solid extensions 810 formed over the area to be occupied by the lyophilized reagent 495. Such extensions 810 connect opposing areas of the well wall 750, thereby retaining the lyophilized reagent 495 at, or adjacent to, the bottom 755 of the well 715. In various embodiments, the well 715 may include any of the various inserts 830, 850, 860, or 870, as discussed above. Alternatively, or in addition thereto, the well wall 750 may be a vertical wall 840 or may be formed to include a screw thread (i.e., a spiral channel) 820. Alternatively, or in addition thereto, the bottom 755 of the well can be formed to include a rough surface, thereby providing sufficient surface area to which the lyophilized reagent 495 will adhere upon formation thereof. Alternatively, or in addition thereto, the lyophilized reagent 495 will adhere to the bottom 755 of the well 715 through a static electrical attractive force created on the well wall 750 and/or bottom 755 of the well 715.

Cartridge With Communicating Wells

Figure 10A:
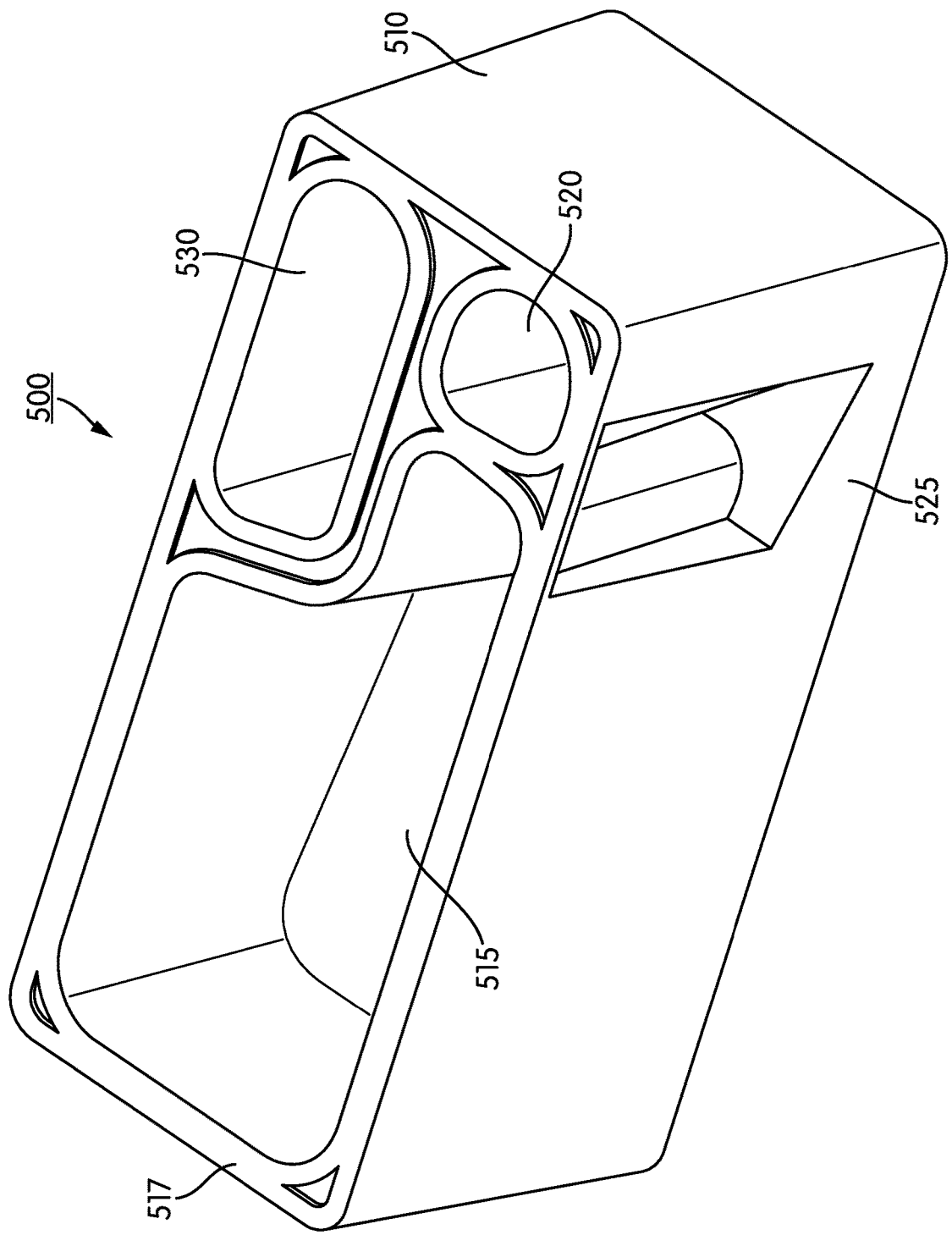
FIGS. 10A and 10B are pictorial diagrams showing perspective views of two cartridges with communicating wells.
Figure 10B:
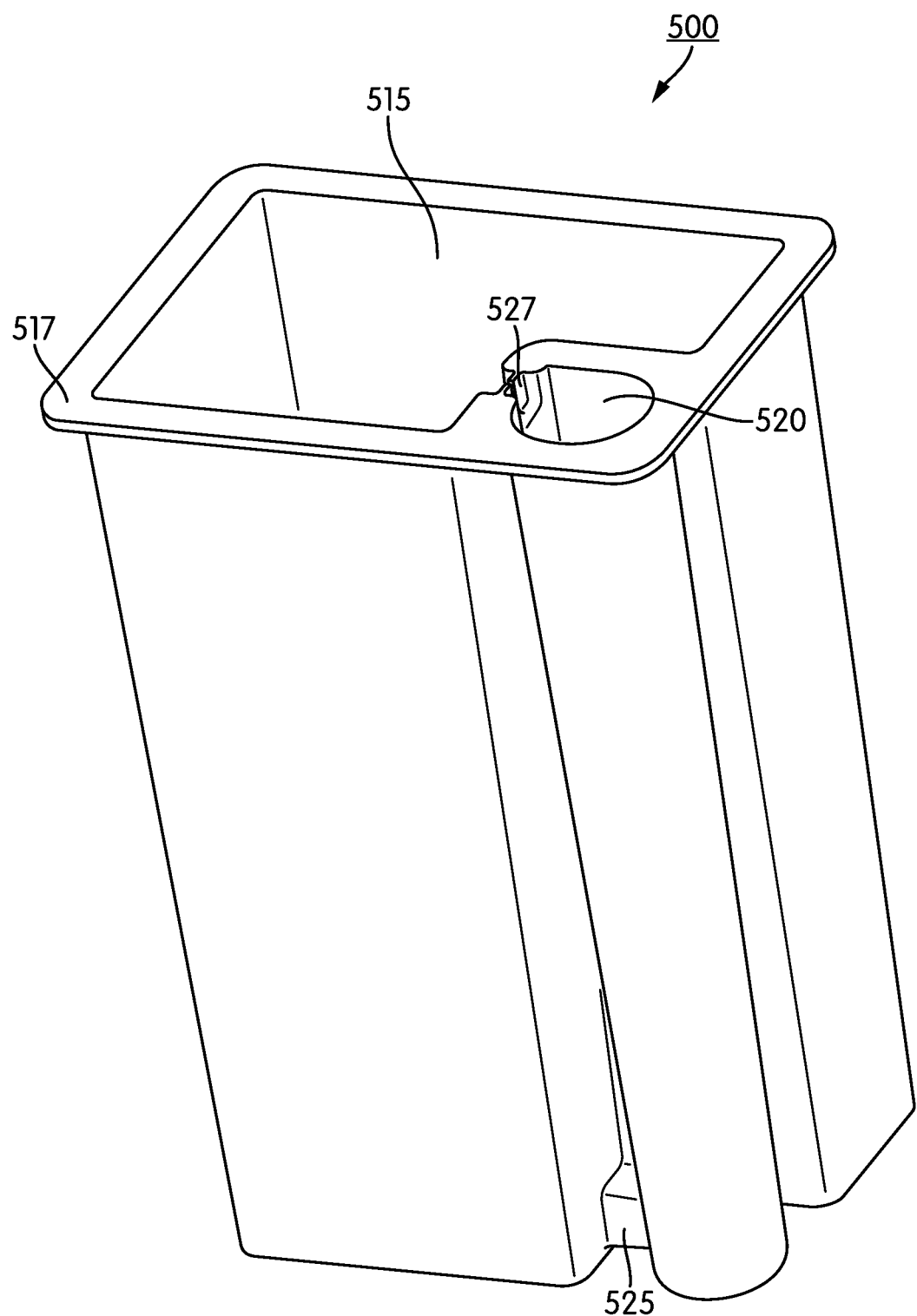

In another aspect of the disclosure, a cartridge 500 with communicating wells for use in an automated process is shown in FIGS. 10A and 10B, which depict different alternative cartridge embodiments. The cartridge 500 includes a casing 510 having a top surface 517, a fluid chamber 520, and a fluid reservoir 515. In various embodiment, the fluid chamber 520 and the fluid reservoir 515 comprise wells open at the top surface 517. In various embodiments, as reflected in the drawings, the fluid chamber 520 has a smaller volumetric capacity than the fluid reservoir 515. As further reflected in the drawings, the perimeter of the open end of the fluid chamber 520 may be smaller than the perimeter of the open end of the fluid reservoir 515, and thus the exposed surface of a fluid in the fluid chamber 520 would be smaller than the exposed surface of a fluid in the fluid reservoir 515.

The fluid chamber 520 and the fluid reservoir 515 may contain the same liquid, such as a diluent or a reconstitution solution for reconstituting the lyophilized reagent (e.g., lyophilized reagent 495).

The cartridge 500 may be provided with one or more fluid connections between the fluid chamber 520 and the fluid reservoir 515. Thus, in various embodiments, one or more openings 525 and/or 527 between the fluid chamber 520 and the fluid reservoir 515 may include one or more channels between the fluid reservoir 515 and the fluid chamber 520 to provide a path through which a liquid or gas may flow between the fluid chamber 520 and the fluid reservoir 515. An opening, such as opening 527, between the fluid chamber 520 and the fluid reservoir 515 may be provided by a slot or hole formed in a wall separating the fluid chamber 520 and the fluid reservoir 515.

In various embodiments, a first opening 525 is provided proximate a lower portion of the fluid chamber 520 and the fluid reservoir 515 (e.g., at a base of the casing 510) for fluid communication between the fluid chamber 520 and the fluid reservoir 515, and a second opening 527 is provided proximate an upper end (i.e., near the open ends) of the fluid chamber 520 and the fluid reservoir 515 for fluid communication between the fluid chamber 520 and the fluid reservoir 515.

As shown in FIG. 10A, the cartridge 500 may also include a second fluid reservoir 530 disposed within the casing and adjacent to the fluid chamber 520. The second reservoir 530 can be utilized to store the same or a different liquid than is stored in reservoir 515. In certain embodiments the second reservoir 530 is not in fluid communication with the fluid reservoir 515 or the fluid chamber 520. In certain embodiments the fluid reservoir 515 and the fluid chamber 520 contain a reconstitution solution, and the second reservoir 530 contains oil.

In various embodiments, each of the fluid chamber 520, fluid reservoir 515, and second reservoir 530 may be sealed with a seal (not shown), such as a metallic foil (or foil laminate). A seal over the fluid reservoir 515, the fluid chamber 520, and/or the second reservoir 530 may be provided to prevent spillage of fluid contents in case cartridge 500 is tipped, dropped, shaken, or inverted, The seal also prevents or retards evaporation of the fluid contents of the sealed reservoir or chamber by preventing or limiting exposure to ambient atmosphere. The seal may further include a plastic liner, such as a thin veneer of HDPE applied to one or both surfaces thereof. The seal may be secured using, for example, a pressure sensitive adhesive or heat seal securing the foil to the top surface 517 securing the seal about the perimeter of the opening of each reservoir or chamber. A plastic liner, such as a thin veneer of HDPE applied to one or both surfaces of the seal, promotes attachment of the frangible seal to the top surface 517 when a heat sealer is used. The one or more openings (525, 527) may also be sealed with a frangible seal to prevent exposure to the ambient atmosphere.

The fluid reservoir 515 and the fluid chamber 520 and any connecting opening(s) are configured so that as fluid is removed from the fluid chamber 520, replacement fluid flows into the fluid chamber 520 from the fluid reservoir 515 (e.g., through an opening 525 provided proximate a lower portion of the fluid chamber 520 and fluid reservoir 515). Moreover, if the fluid reservoir is sealed, one or more conduits may be provided to permit air to flow into the fluid reservoir 515 (e.g., through an opening 527 provided proximate an upper portion of the fluid chamber 520 and fluid reservoir 515) as fluid is drawn out of the fluid reservoir 515 to thereby allow the pressure in the reservoir to equilibrate.

The chamber 520 is may be sealed with a frangible seal that is puncturable by a pipette tip. The entire volume of fluid in the fluid chamber 520 and the fluid reservoir 515 is accessible to a fluid transfer apparatus, but a relatively small surface area of that fluid—e.g., corresponding to the width of the chamber 520 or to the size of a puncture hole formed in a seal over the chamber 520—is exposed to air. Thus, the configuration of the cartridge 500 retards evaporation of fluids contained therein.

An amount of liquid, such as reconstitution solution, may be removed from the fluid chamber 520 within an automated pipettor and transferred to a well (e.g., well 430 or 715) to reconstitute a lyophilized reagent (e.g., lyophilized reagent 495), as described below.

The cartridge 500 may be constructed of an injection molded plastic, such as the plastics described above. As discussed above, the plastic used to form the cartridge 500 may be one having low permeability to air and/or moisture.

Any exterior surface of the cartridge 500 may further include one or more identifying labels, such as a barcode, 2D barcode, quick response (QR) code, radio frequency identification (RFID), or other human or machine readable indicia, disposed thereon. The information carried on such label may include identifying information regarding the cartridge 500, including information regarding the liquids/reagents contained therein, such as lot number, serial number, assay type, expiration date, etc.

Cartridge Rack

Figure 11A:
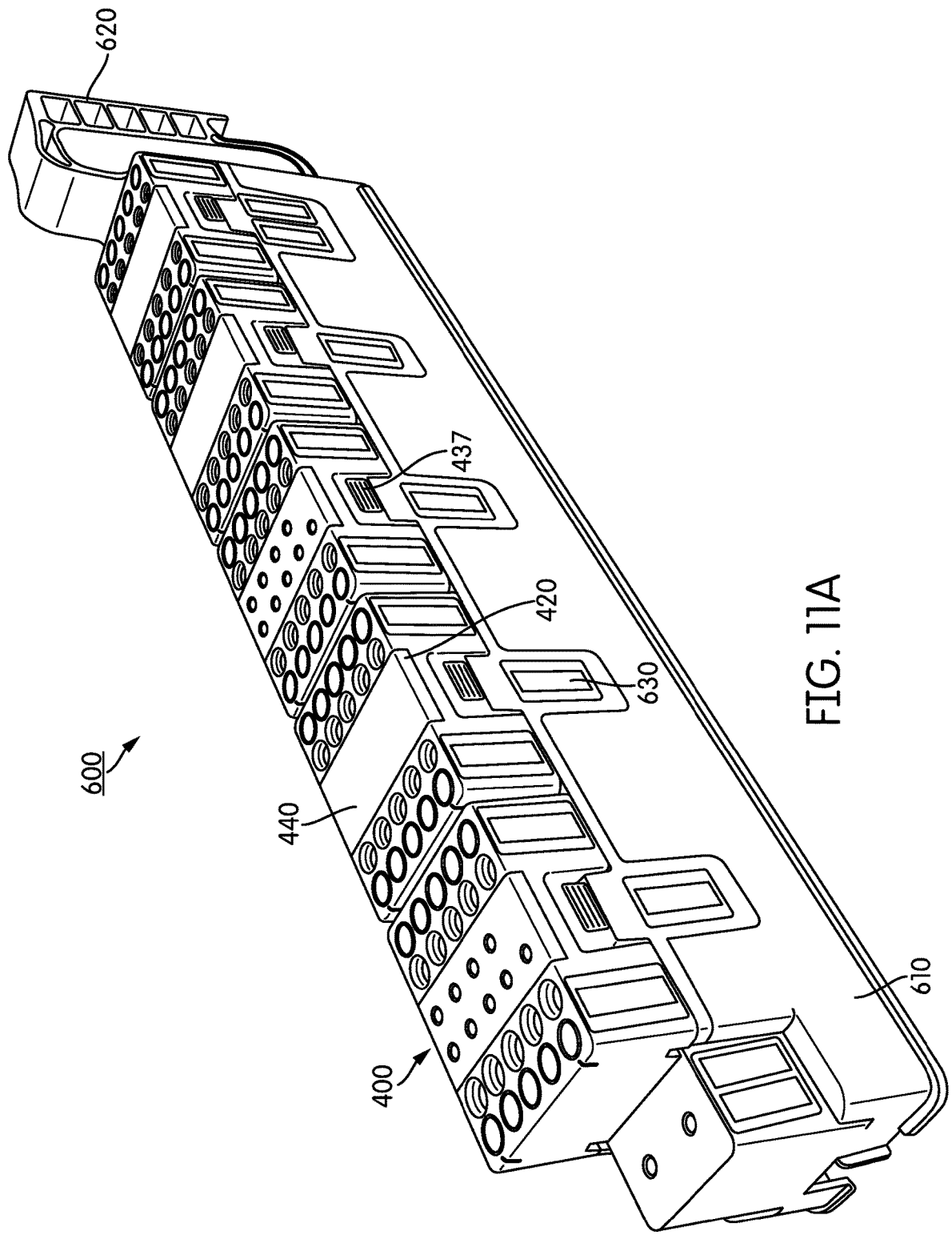
FIGS. 11A-11D are pictorial diagrams showing a cartridge rack.
Figure 11B:
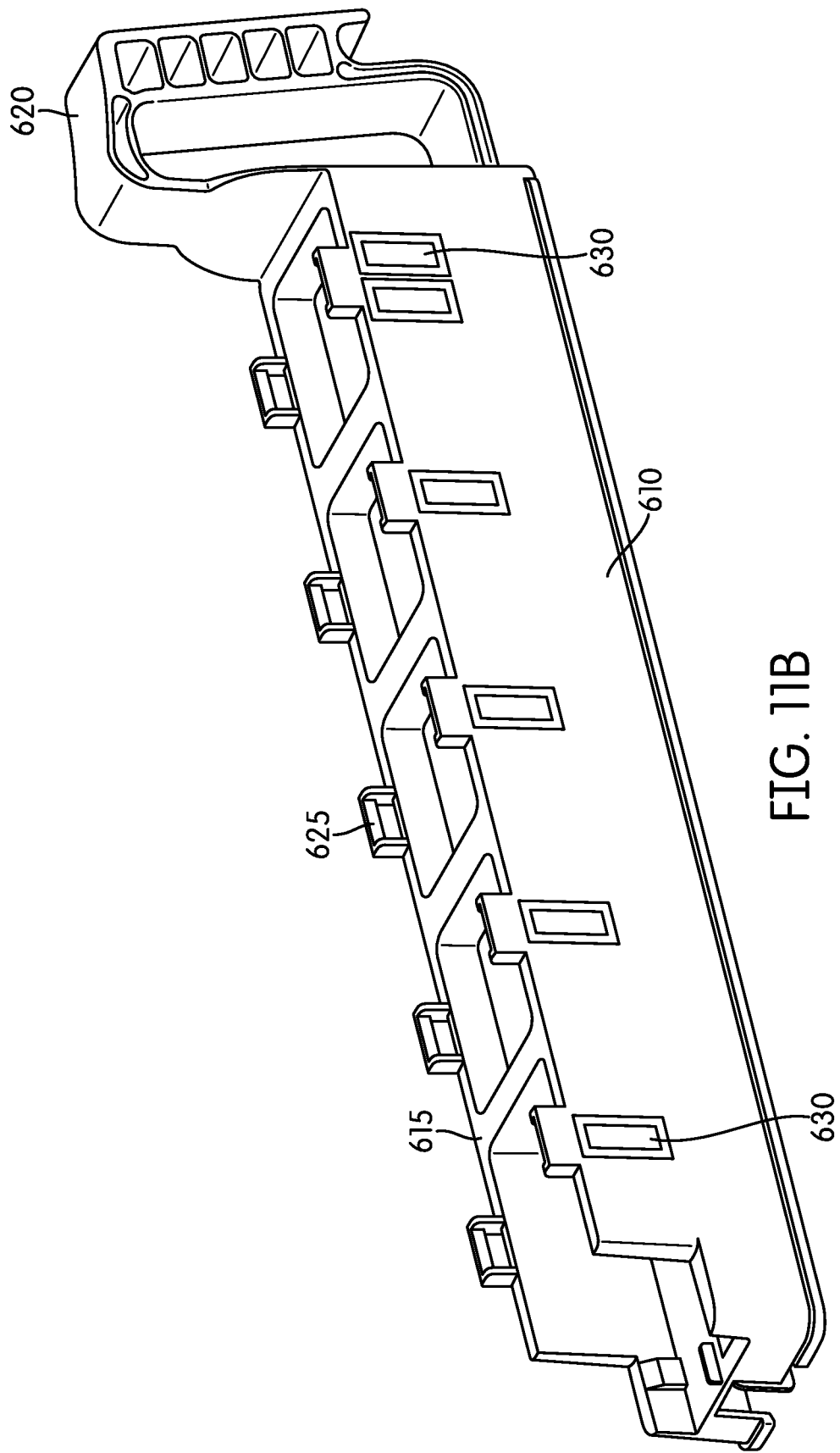
Figure 11C:
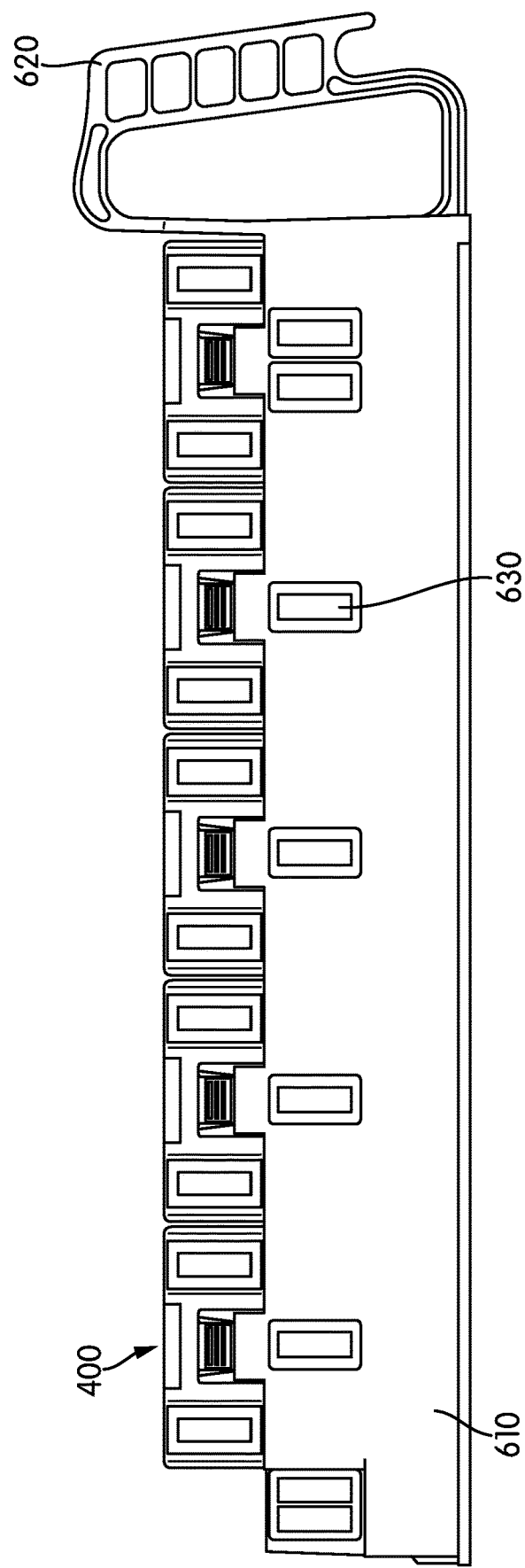
Figure 11D:
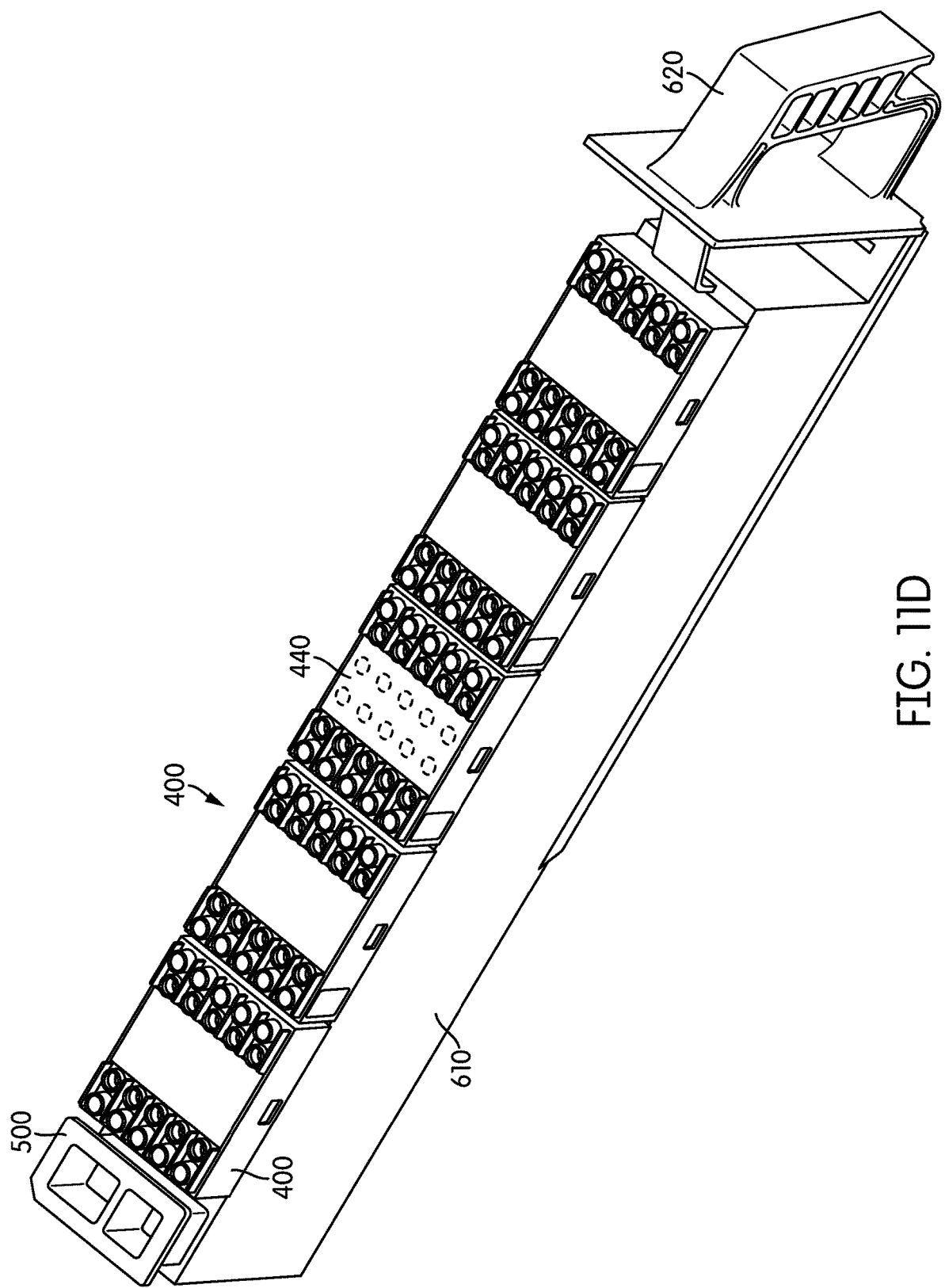

In another aspect, disclosed herein is a cartridge rack for use in an automated process. With reference now to FIGS. 11A-11D, the cartridge rack 600 includes a chassis 610 and a handle 620. A top surface 615 of the chassis 610 is configured for releasable attachment of one or more multi-well trays 400 thereto, and therefore may include a plurality of locking members 625 for releasably engaging the locking fingers 422 of the multi-well tray 400 (see FIG. 6A). While the FIG. 11B shows that two locking members 625 are provided for each multi-well tray 400, it should be understood that the number of locking members 625 provided for each multi-well tray 400 will correspond with the number of locking fingers 422 provided on the multi-well tray 400 to be attached thereto.

Disposed on a surface of the chassis 610 is a plurality of identifying labels such as machine readable indicia 630, such as a barcode, 2D barcode, quick response (QR) code, radio frequency identification (RFID), or other human or machine readable indicia, disposed thereon. The information carried on such label may include identifying information regarding the cartridge rack 600, multi-well tray(s) 400 attached thereto, and/or the card insert(s) 420 attached to the multi-well tray(s) 400, and/or the multi-well tray 400 position on the rack. The machine readable indicia 630 may be readable through a direct contact connection, a wired connection, or a wireless connection between the cartridge rack 600 on the automated biochemical analyzer.

In various embodiments, the chassis 610 is configured for releasable attachment of two or more multi-well trays 400 thereto, and may further be configured for releasable attachment to a cartridge with communicating wells 500. Thus, in an exemplary embodiment, five multi-well receptacles 400 and one cartridge 500 may be releasably attached to the chassis 610 for use in an automated biochemical analyzer. However, 2, 3, 4, 5, 6, 7, or 8 multi-well trays 400, and/or 1, 2, 3, or 4 cartridges 500 may be attached to the chassis 610.

System for Automated Reagent-Based Assay

In another aspect, the present disclosure provides a system for an automated reagent-based assay. The system includes a multi-well tray 400 that includes a plurality of wells 430, a cartridge with communicating wells 500, and an automated pipettor positioned on a robot arm (not shown). The system includes a housing within which each of the components are located. Each well 430 of the multi-well tray 400 shown and discussed above contains a lyophilized reagent 495 and is arranged in alignment with each other. The wells 430 of the multi-well tray 400 may be sealed with a frangible seal. The multi-well tray 400 may further include a plurality of additional wells 415, 416 provided for receiving a receptacle 100 and a cap 200. When present, the additional wells are positioned in aligned pairs, and the pairs are positioned in alignment with at least one well 430 containing a reagent, such as a lyophilized reagent 495. Thus, the multi-well tray 400 may contain a plurality of sets 435 of wells, where a first well 415 contains a cap 200, a second well 416 contains a receptacle 100, and a third well contains a reagent such as a lyophilized reagent 495.

The cartridge with communicating wells 500 includes a casing 510 having a top surface 517, a fluid chamber 520. A first opening 527 is provided in the top surface of the casing having at least one side wall surface extending to, or optionally forming at least a portion of, the fluid chamber. A fluid reservoir 515 is disposed within the casing and in fluid communication with the fluid chamber. In certain embodiments, the cartridge 500 will also include a second reservoir 530 that is disposed within the casing 510 and adjacent to the fluid chamber 520.

The automated pipettor is positioned on a robot arm contained in an automated biochemical analyzer. The automated pipettor is adapted to execute a retrieval and dispense protocol for conducting biochemical reactions. The retrieval and dispense protocol may be performed by a controller (not shown) electrically connected to the robot arm and/or the automated pipettor to retrieve a portion of the reagent from the cartridge 500 and dispense the portion of the reagent into one or more wells of the multi-well tray 400, 700 or into one or more receptacles. The retrieval and dispense protocol may then be repeated for automated dispensing of the reagent into each of remaining wells of the multi-well tray 400.

In one exemplary embodiment, the automated pipettor will receive a command to perform automated actions required for performing an automated reagent-based assay. The automated pipettor is then moved by the robot arm to a position over an unused pipette tip 310 and is lowered to enable frictional attachment thereto. Once the automated pipettor, having the pipette tip 310 attached thereto, is raised such that the pipette tip 310 is not obstructed by additional unused tips and/or other components within the automated biochemical analyzer, the robot arm moves the automated pipettor into a designated position over a cartridge 500. The automated pipettor is thereafter lowered into the fluid chamber of the cartridge 500. If present, a frangible seal covering the fluid chamber is punctured by the pipette tip 310. The automated pipettor then withdraws a predetermined amount of diluent and is raised such that the pipette tip 310 is unobstructed by the cartridge 500 and/or other components within the automated biochemical analyzer.

The robot arm then moves the automated pipettor into a designated position over a spatially indexed multi-well tray 400 and then lowers the pipettor such that the pipette tip 310 punctures a frangible seal 440 (if present) covering a well 430 disposed in the card insert 420 attached to the base 410 of the multi-well tray 400. The diluent is then deposited into the well 430 containing a lyophilized reagent 495 used in the reagent-based assay. Optionally, the automated pipettor will repeatedly aspirate and the dispense the liquid contained in the well 430 to allow sufficient time and fluidic pressure required to reconstitute the lyophilized reagent 495. The automated pipettor thereafter collects the reconstituted reagent and withdraws the pipette tip 310 from the well 430 of the multi-well tray 400 such that the pipette tip 310 is unobstructed by the well 430 and/or other components within the automated biochemical analyzer. The robot arm then moves the automated pipettor into a second designated position over the spatially indexed multi-well tray 400. The second position is selected in accordance with the set 435 of wells to which the well 430 of the card insert belongs. The automated pipettor is then lowered into a well 416 containing a receptacle 100, which may or may not contain a sample undergoing analysis. Optionally, when a sample undergoing analysis is present in the receptacle 100, the automated pipettor will repeatedly aspirate and then dispense the liquid contained in the receptacle 100 to allow sufficient time and fluidic pressure required to mix the contents of the receptacle 100 within the well 416, thereby creating a reaction mixture.

After optional mixing, the automated pipettor withdraws the pipette tip 310 from the well 416, but leaves the reaction mixture within the receptacle 100. The robot arm then moves the automated pipettor to a location over a waste receptacle and ejects the pipette tip 310. After ejection, the robot arm moves the automated pipettor to a third designated position over the spatially indexed multi-well tray 400. The third position is selected in accordance with the set 435 of wells to which the first and second wells belong. The automated pipettor is then lowered into the third well 415 containing a cap 200 to enable frictional attachment thereto. Once the automated pipettor having the cap 200 attached thereto is raised such that the cap 200 is not obstructed the well 415 and/or other components within the automated biochemical analyzer, the robot arm moves the automated pipettor into the second designated position over the well 416 containing the receptacle 100 containing the reaction mixture. The automated pipettor is then lowered such that the cap 200 is securably attached to the receptacle 100 as described above. As the automated pipettor withdraws from the well 416, the capped receptacle attached thereto is withdrawn from the well 416 of the multi-well tray 400 for transport to, for example, a thermocycler for automated incubation.

In another exemplary embodiment, the automated pipettor will receive a command to perform automated actions required for performing an automated reagent-based assay. The automated pipettor is then moved by the robot arm to a position over an unused pipette tip 310, and is lowered to enable frictional attachment thereto. Simultaneously, prior to, or after such movement, a transport mechanism, such as a rotary distributor (not shown) within the biochemical analyzer attaches to an arm 720 of a multi-well tray 700 and transports the multi-well tray 700 to a predetermined position for use in the analysis.

Once the automated pipettor, having the pipette tip 310 attached thereto, is raised such that the pipette tip 310 is not obstructed by additional unused tips and/or other components within the automated biochemical analyzer, the robot arm moves the automated pipettor into a designated position over a cartridge 500. The automated pipettor is thereafter lowered into the oil chamber 530 of the cartridge 500. If present, a frangible seal covering the oil chamber 530 is punctured by the pipette tip 310. The automated pipettor then withdraws a predetermined amount of oil and is raised such that the pipette tip 310 is unobstructed by the cartridge 500 and/or other components within the automated biochemical analyzer.

The robot arm then moves the automated pipettor into a designated position over a spatially indexed multi-well tray 400 and/or over a receptacle 100, and the pipettor is lowered such that the pipette tip 310 enters the open end 145 thereof. The oil is then dispensed into the receptacle 100. Optionally, the procedure of withdrawing oil from the oil chamber 530 of the cartridge 500 is repeated one or more times, depending on the number of reactions to be performed.

Thereafter, the automated pipettor withdraws the pipette tip 310 from the receptacle 100, and the robot arm moves the automated pipettor to a location over a waste receptacle and ejects the pipette tip 310. After ejection, the robot arm moves the automated pipettor to a position over a second unused pipette tip 310 and lowers the pipettor to enable frictional attachment thereto. Once the automated pipettor, having the second pipette tip 310 attached thereto, is raised such that the pipette tip 310 is not obstructed by additional unused tips and/or other components within the automated biochemical analyzer, the robot arm moves the automated pipettor into a designated position over a second receptacle 100 having therein a sample for analysis, and is lowered such that the pipette tip 310 enters the open end 145 thereof. The sample is then collected from the second receptacle and transferred to the first receptacle 100. It should be understood that in certain embodiments, the sample will have been previously dispensed into the receptacle prior to deposit of the oil and/or the sample for analysis may be transferred from a material transfer unit (not shown) within the biochemical analyzer. After depositing the sample into the first receptacle, the automated pipettor withdraws the pipette tip 310 from the receptacle 100, and the robot arm moves the automated pipettor to a location over a waste receptacle and ejects the pipette tip 310. After ejection, the robot arm moves the automated pipettor to a position over a third unused pipette tip 310 and lowers the pipettor to enable frictional attachment thereto.

Once the automated pipettor having the third pipette tip 310 attached thereto is raised such that the pipette tip 310 is not obstructed by additional unused tips, and/or other components within the automated biochemical analyzer, the robot arm moves the automated pipettor into the second designated position over the cartridge 500 and lowers the pipettor into the fluid chamber 520 of the cartridge 500. If present, a frangible seal covering the fluid chamber 520 is punctured by the pipette tip 310. The automated pipettor then withdraws a predetermined amount of diluent and is raised such that the pipette tip 310 is unobstructed by the cartridge 500 and/or other components within the automated biochemical analyzer.

The robot arm then moves the automated pipettor into a designated position over a spatially indexed multi-well tray 700 and lowers the pipettor such that the pipette tip 310 punctures a frangible seal (if present) covering a well 715 disposed in the multi-well tray 700. The diluent is then deposited into the well 715 containing a lyophilized reagent 495 used in the reagent-based assay. Optionally, the automated pipettor will repeatedly aspirate and dispense the liquid contained in the well 715 to allow sufficient time and fluidic pressure required to reconstitute the lyophilized reagent 495.

The automated pipettor thereafter collects the reconstituted reagent and withdraws the pipette tip 310 from the well 715 of the multi-well tray 700 such that the pipette tip 310 is unobstructed by the well 715 and/or other components within the automated biochemical analyzer. The robot arm then moves the automated pipettor into the designated position over the first receptacle 100 containing the dispensed oil and sample for analysis. The automated pipettor is then lowered into the open end 145 of the receptacle 100 to dispense the reconstituted reagent. Optionally, the automated pipettor will repeatedly aspirate and dispense the liquid contained in the receptacle 100 to allow sufficient time and fluidic pressure required to mix the contents of the receptacle 100, thereby creating a reaction mixture.

After optional mixing, the automated pipettor withdraws the pipette tip 310 from the receptacle 100, but leaves the reaction mixture within the receptacle 100. The robot arm then moves the automated pipettor to a location over the waste receptacle and ejects the pipette tip 310. After ejection, the robot arm moves the automated pipettor to a designated position over a well 415 containing a cap 200 to enable frictional attachment thereto. Once the automated pipettor having the cap 200 attached thereto is raised such that the cap 200 is not obstructed the well 415 and/or other components within the automated biochemical analyzer, the robot arm moves the automated pipettor into the designated position over the receptacle 100 containing the reaction mixture. The automated pipettor is then lowered such that the cap 200 is securably attached to the receptacle 100. As the automated pipettor is raised, the capped receptacle is lifted from a receptacle holder or well of a multi-well tray 400 for transport to, for example, a centrifuge and/or thermocycler for automated incubation.

In certain embodiments, it is desirable to expedite the process of reconstitution of the lyophilized reagent 495, mixing of the reagent with the test sample, and subsequent capping of the receptacle 100 containing the reagent mixture. In such embodiments, more than one robot arm and automated pipettor may be provided within the automated biochemical analyzer, and may be independently controlled to expand the capabilities thereof. Alternatively, or in addition thereto, the automated biochemical analyzer may include one or more pick and place robots, which may be used to perform functions not related to collection and/or deposit of liquids, such as capping of a receptacle 100 containing a reaction mixture and/or transport of the capped receptacle to a centrifuge and/or thermocycler for automated incubation.

Although the present disclosure has been described with reference to the above example, it will be understood that modifications and variations are encompassed within the spirit and scope of the disclosed subject matter. Accordingly, the present disclosure is limited only by the following claims.

What is claimed is:

1. A method for reconstituting a lyophilized reagent contained within a reagent well having an internal side wall, a bottom wall, and an open upper end, the method comprising the steps of:
   drawing a diluent into a pipette tip attached to an automated pipettor; and
   dispensing the diluent into the reagent well containing the lyophilized reagent, wherein the reagent well includes one or more retention features disposed about the periphery of the internal side wall and defining a central opening into the well, wherein the one or more retention features are integrally formed with the internal side wall, wherein each of the one or more retention features extends over a portion of the lyophilized reagent, thereby retaining the lyophilized reagent within the reagent well, and wherein the one or more retention features are configured and arranged to permit passage of the pipette tip through the central opening into the reagent well.

2. The method of claim 1, further comprising, after the dispensing step, the steps of aspirating and dispensing the contents of the reagent well one or more times with the automated pipettor to produce a reconstituted form of the reagent, wherein the aspirating and dispensing steps occur within the reagent well.

3. The method of claim 2, further comprising, after the aspirating and dispensing steps, the steps of withdrawing at least a portion of the reconstituted reagent from the reagent well and transferring the withdrawn reconstituted reagent to a different receptacle.

4. The method of claim 1, wherein a frangible seal is affixed to a top surface of the reagent well and covers the open upper end of the reagent well, and further comprising, prior to the dispensing step, the step of puncturing the frangible seal with the pipette tip.

5. The method of claim 1, wherein the one or more retention features consist of an annular ridge formed on the internal side wall of the reagent well.

6. The method of claim 1, wherein the one or more retention features consist of a spiral channel formed along a length of the internal side wall of the reagent well.

7. The method of claim 1, wherein the one or more retention features consist of a set of longitudinally extending and circumferentially-spaced rigid guides projecting radially from the internal side wall of the reagent well.

8. The method of claim 1, further comprising, after the dispensing step, the steps of withdrawing a reconstituted form of the reagent from the reagent well and transferring the reconstituted reagent to a different receptacle.

9. The method of claim 8, wherein the one or more retention features consist of a set of longitudinally extending and circumferentially-spaced rigid guides projecting radially from the internal side wall, and wherein the rigid guides direct the pipette tip toward the axial center of the reagent well as the pipette tip is inserted into the reagent during the withdrawing step.

10. The method of claim 8, wherein the reagent well includes one or more features formed in the bottom wall of the reagent well to facilitate the deposit and/or collection of a fluid from the reagent well, and the withdrawing step comprises contacting the features with a distal end of a pipette tip inserted into the reagent well, thus preventing a distal end of the pipette tip from making sealing contact with the bottom wall of the reagent well.

11. The method of claim 10, wherein the one or more features formed in the bottom wall of the reagent well comprise one or more of one or more grooves, a pair of crisscrossed grooves, one or more ridges, an annular ridge, and a plurality of bumps.

12. The method of claim 8, wherein the one or more retention features consist of an annular ridge formed on the internal side wall of the reagent well.

13. The method of claim 8, wherein the one or more retention features consist of a spiral channel formed along a length of the internal side wall of the reagent well.

* * * * *